(12) United States Patent
Rao et al.

(10) Patent No.: US 9,849,198 B2
(45) Date of Patent: Dec. 26, 2017

(54) DISCRETE IMAGING OF HEPATIC OXIDATIVE AND NITROSATIVE STRESS WITH TWO-CHANNEL NANOPARTICLES FOR IN VIVO DRUG SAFETY SCREENING

(71) Applicant: The Board of Trustees of the Leland Stanford Junior University, Palo Alto, CA (US)

(72) Inventors: Jianghong Rao, Sunnyvale, CA (US); Kanyi Pu, Mountain view, CA (US); Adam Shuhendler, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 674 days.

(21) Appl. No.: 14/321,873

(22) Filed: Jul. 2, 2014

(65) Prior Publication Data
US 2015/0011878 A1    Jan. 8, 2015

Related U.S. Application Data

(60) Provisional application No. 61/841,958, filed on Jul. 2, 2013.

(51) Int. Cl.
*A61K 9/14*    (2006.01)
*A61K 49/00*   (2006.01)
*A61B 5/00*    (2006.01)
*A61B 5/1473*  (2006.01)

(52) U.S. Cl.
CPC ........ *A61K 49/0093* (2013.01); *A61B 5/0071* (2013.01); *A61B 5/14735* (2013.01); *A61B 5/4244* (2013.01); *A61B 5/4848* (2013.01); *A61K 49/0054* (2013.01)

(58) Field of Classification Search
None
See application file for complete search history.

(56) References Cited

U.S. PATENT DOCUMENTS

| | | |
|---|---|---|
| 5,668,648 A | 9/1997 | Saito et al. |
| 5,707,804 A | 1/1998 | Mathies et al. |
| 5,728,528 A | 3/1998 | Mathies et al. |
| 5,853,992 A | 12/1998 | Glazer et al. |
| 5,869,255 A | 2/1999 | Mathies et al. |

OTHER PUBLICATIONS http://beta.merriam-webster.com/dictionary/derivative Printed From Web Dec. 9, 2015.*

* cited by examiner

*Primary Examiner* — James Rogers
(74) *Attorney, Agent, or Firm* — Thomas | Horstemeyer, LLP

(57) ABSTRACT

Encompassed are embodiments of activatable nanoprobes useful for in vivo longitudinal imaging of drug hepatotoxicity with oxidative and nitrosative stress as the safety biomarkers. Both $H_2O_2$ and $ONOO^-$ are important mediators of radical stress. Two channels of optical detection, intrinsically free from cross-talk, were engineered into superconducting polymer nanoparticles to generate chemiluminescence resonance energy transfer between the conjugated polymer matrix of the nanoparticle and an incorporated chemiluminescent substrate allowing for the luminescent detection of $H_2O_2$ and fluorescence resonance energy transfer between the polymer matrix and an oxidation-degradable fluorophore for ratiometric detection of ONOO These nanoprobes have been applied for real-time in vivo monitoring of hepatotoxicity resulting from challenges from drugs. In addition to the ability of imaging the dose-dependence of oxidative and nitrosative stress, the positive detection of radical stress that precedes histological changes allow the early and longitudinal detection of drug-induced hepatotoxicity in vivo.

6 Claims, 27 Drawing Sheets

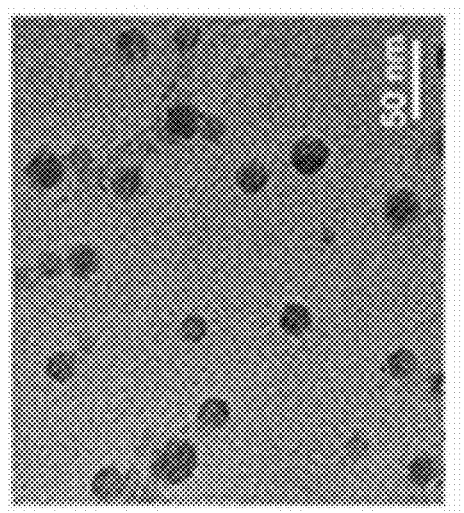
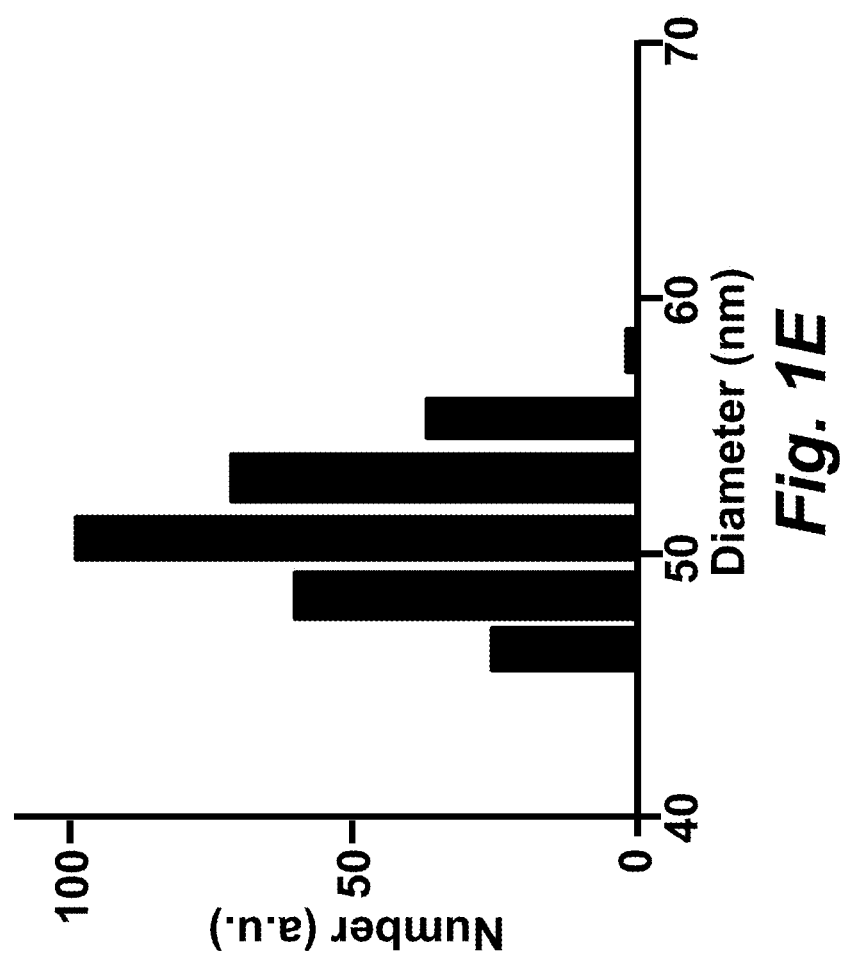
Fig. 1F
Fig. 1E

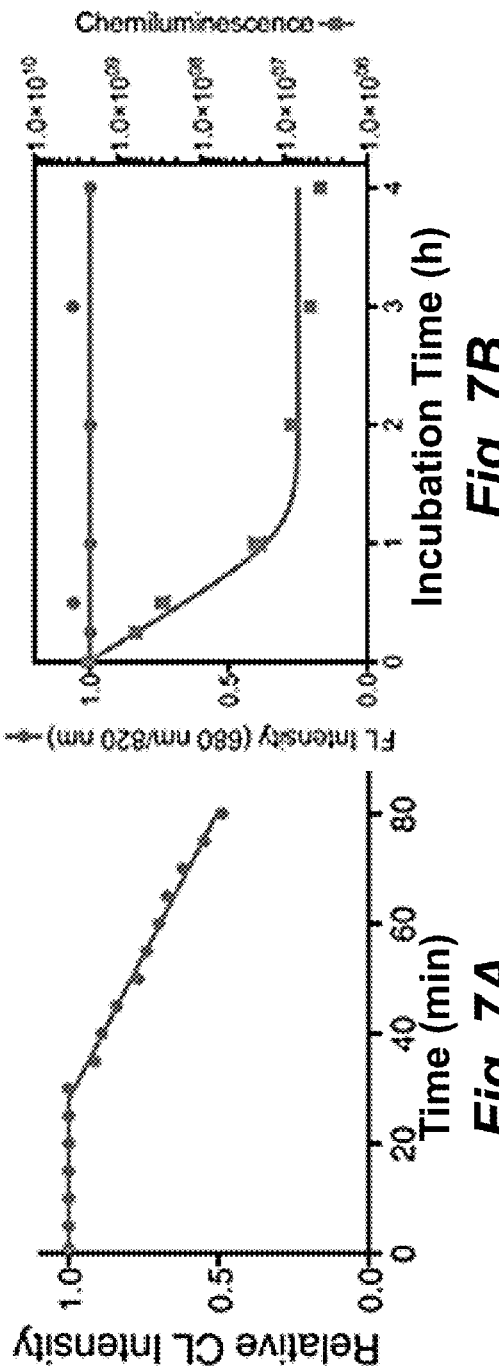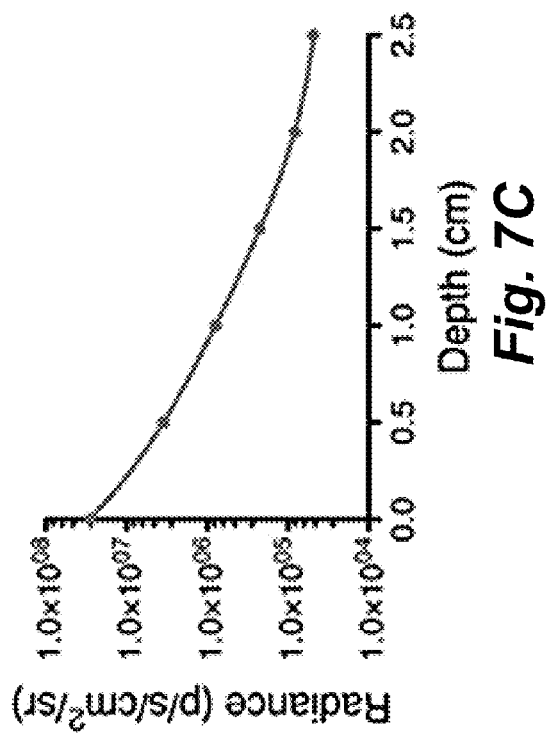
Fig. 7A
Fig. 7B
Fig. 7C

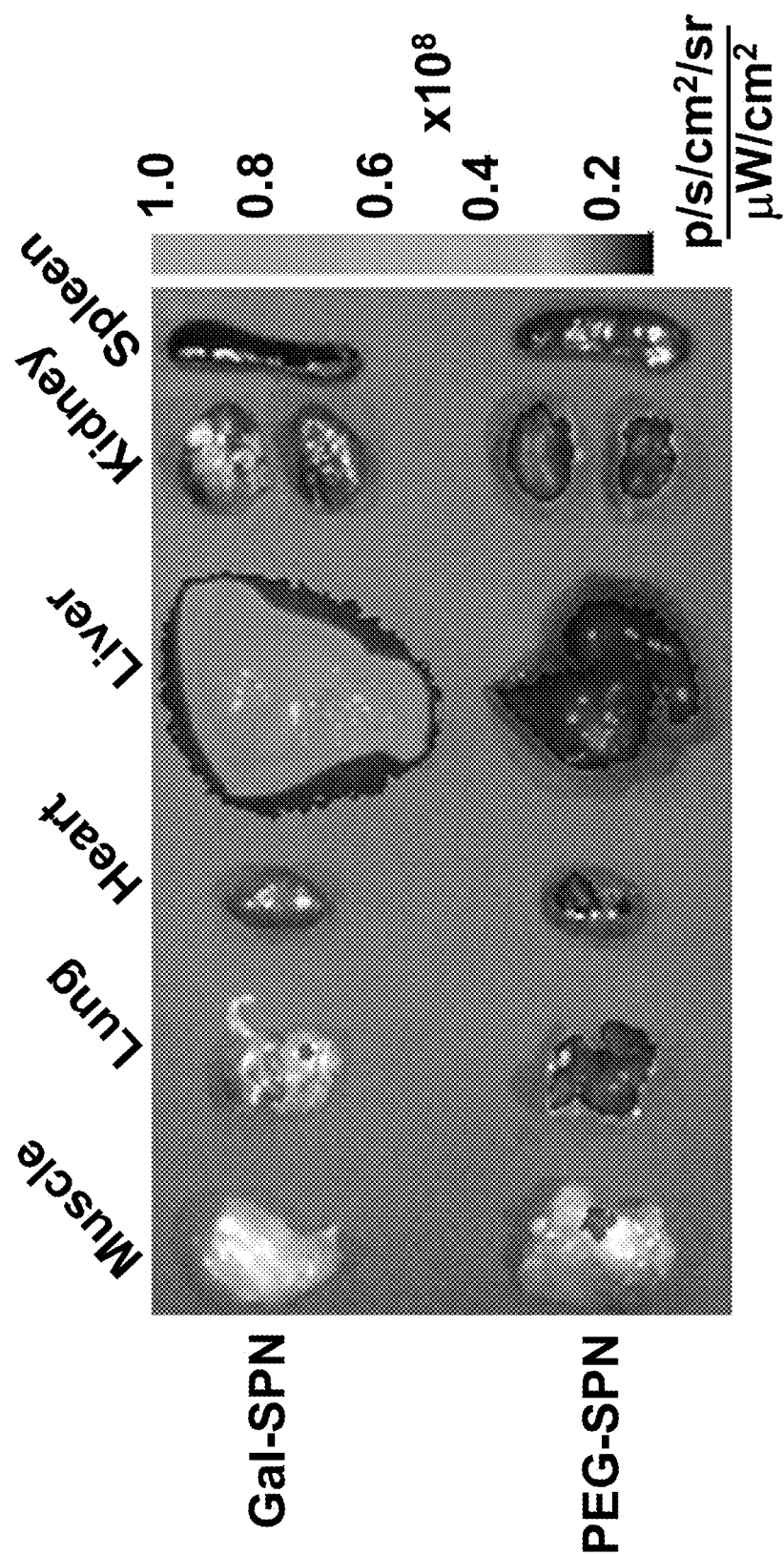

Diaminocyanine

PFODBT

DISCRETE IMAGING OF HEPATIC OXIDATIVE AND NITROSATIVE STRESS WITH TWO-CHANNEL NANOPARTICLES FOR IN VIVO DRUG SAFETY SCREENING

CROSS-REFERENCE TO RELATED APPLICATIONS

This application claims priority to U.S. Provisional Patent Application Ser. No. 61/841,958 entitled "DISCRETE IMAGING OF HEPATIC OXIDATIVE AND NITROSATIVE STRESS WITH TWO-CHANNEL NANOPARTICLES FOR IN VIVO DRUG SAFETY SCREENING" and filed Jul. 2, 2013, the entirety of which is hereby incorporated by reference.

STATEMENT REGARDING FEDERALLY SPONSORED RESEARCH OR DEVELOPMENT

This invention was made with Government support under contracts 2R01 DK099800-06A1, R01CA135294, and R21CA138353A2 awarded by the National Institutes of Health. The government has certain rights in the invention.

FIELD OF THE DISCLOSURE

The present disclosure relates to a modular nanoparticle platform capable of simultaneous and differential dual analyte sensing using two-optical channels substantially free from cross-talk. The present disclosure further relates to a method for in vivo and longitudinal imaging capable of the simultaneous and differential detection of drug-induced hepatic oxidative and nitrosative stress.

BACKGROUND

Drug toxicity is a pertinent and long-standing concern of modern medicine (Nasr et al., (2011) *Adv. Ther.* 28: 842-856). In the United States alone, an estimated 750,000 emergency department visits per year are due to unintentional drug toxicity from both prescription and over-the-counter medicines, with more than two-thirds occurring after therapeutic drug use (Budnitz et al., (2006) *JAMA* 296: 1858-1866). Of the organ systems affected, the liver was most frequently implicated with a 60-80% mortality rate in the absence of liver transplant (Sakatis et al., (2012) *Chem. Res. Toxicol.* 25: 2067-2082; Srivastava et al., (2010) *Handbook Exp. Pharmacol.* pp 165-194). In addition to its effects on the end-user, drug-induced hepatotoxicity bears broad and direct implications for the productive innovation of pharmacotherapeutics.

The rising costs of clinical trials, estimated at $1.9 billion for 2013 (Willmann et al., (2008) *Nat. Rev. Drug Discov.* 7: 591-607), in conjunction with 90% attrition rates (Willmann et al., (2008) *Nat. Rev. Drug Discov.* 7: 591-607; Rudin, M. (2009) *Curr. Opin. Chem. Biol.* 13: 360-371; Tengowski & Kotyk (2005) *Prog. Drug. Res.* 62: 257-278; Wang & Yan (2008) *Lab Anim.* 42: 433-441) makes drug development an ever more risky endeavour (Kola & Landis (2004) *Nat. Rev. Drug Discov.* 3: 711-715). Even after approval is granted, the pharmaceutical industry is faced with an increasing number of drug withdrawals from the market (Sakatis et al., (2012) *Chem. Res. Toxicol.* 25: 2067-2082; Kola & Landis (2004) *Nat. Rev. Drug Discov.* 3: 711-715).

Two decades ago 40% of drug candidate attrition was due to poor pharmacokinetics and bioavailability. However, the implementation of high sensitivity liquid chromatography-mass spectrometry assays in pre-clinical evaluation saw this cause of attrition drop to below 10% by 2000 (Kola & Landis (2004) *Nat. Rev. Drug Discov.* 3: 711-715; Kramer et al., (2007) *Nat. Rev. Drug Discov.* 6: 636-649). Thus, the adoption of novel methodologies by the pharmaceutical industry as early as possible in the drug development process has historically remediated attrition rates and improved drug development outcomes (Kola & Landis (2004) *Nat. Rev. Drug Discov.* 3: 711-715). To this end, since drug-induced hepatotoxicity is the single most important cause of both FDA non-approval and withdrawal from the market after approval, a reduction in the cost and risk of drug development may be possible through innovative pre-clinical hepatotoxicity screening methods (Sakatis et al., (2012) *Chem. Res. Toxicol.* 25: 2067-2082; Tengowski & Kotyk (2005) *Prog. Drug. Res.* 62: 257-278; Wang & Yan (2008) *Lab Anim.* 42: 433-441; Kola & Landis (2004) *Nat. Rev. Drug Discov.* 3: 711-715; Dimasi, J. A. (2001) *Clin. Pharmacol. Ther.* 69: 297-307; Reese et al. (2011) *Chem. Biol. Interact.* 192: 60-64). Importantly, new robust methods for the pre-clinical interrogation of drug hepatotoxicity can also have added benefits of improving end-user safety and therapeutic outcomes (Kola & Landis (2004) *Nat. Rev. Drug Discov.* 3: 711-715; Kramer et al., (2007) *Nat. Rev. Drug Discov.* 6: 636-649).

SUMMARY

The disclosure encompasses embodiments of nanoprobe molecular imaging technology incorporating a modular nanoparticle platform capable of simultaneous and differential dual analyte sensing using two-optical channels substantially free from cross-talk. Further provided is a method for in vivo and longitudinal imaging capable of the simultaneous and differential detection of drug-induced hepatic oxidative and nitrosative stress. The correlation of in vivo-generated oxidative and nitrosative stress imaging with histological markers of hepatotoxicity validate ROS and RNS as prodromal imaging biomarkers for drug safety evaluation.

One aspect of the disclosure, therefore, encompasses embodiments of a bifunctional nanoprobe for detecting hepatic injury due to a at least one of a reactive oxygen species and a reactive nitrogen species, said nanoprobe comprising: (i) a matrix core comprising: (a) a fluorescent superconducting polymer; and (b) a copolymer having a plurality of galactose moieties conjugated thereto, wherein the galactose moieties are disposed at the surface of the matrix core; (ii) a chemiluminescent sensor that in the presence of hydrogen peroxide can provide a chemical source of energy capable of inducing a detectable signal from a dye; and (iii) a fluorescent sensor that is decomposed when in the presence of a reactive oxygen or nitrogen species.

In embodiments of this aspect of the disclosure, the fluorescent superconducting polymer can be poly[2,7-(9,9-di-octyl-fluorene)-alt-4,7-bis(thiophen-2-yl)benzo-2,1,3-thiadiazole].

In embodiments of this aspect of the disclosure, the copolymer can comprise polystyrene and polyethylene glycol monomers, wherein the galactose moieties can be conjugated to the polyethylene glycol.

In embodiments of this aspect of the disclosure, the fluorescent sensor can be, but is not limited to, 2-[4'-(β-carboxyethylthio)-7'-(1",3",3"-trimethylindolenine)-3',5'-trimethyleneheptatrien-1-yl]-1,3,3-trimethylindolenium perchlorate (IR775S).

In embodiments of this aspect of the disclosure, the chemiluminescent sensor can be bis-(2,4,5-trichloro-6-(pentyloxycarbonyl)phenyl)oxalate (CPPO).

Another aspect of the disclosure encompasses embodiments of a method of detecting hepatic injury in a human or non-human subject, said method comprising the steps of: (a) delivering to the liver of a human or non-human subject a pharmaceutically acceptable composition comprising a bifunctional nanoprobe for detecting hepatic injury and a pharmaceutically acceptable carrier, said nanoprobe comprising: (i) a matrix core comprising: (a) a fluorescent superconducting polymer; and (b) a copolymer having a plurality of galactose moieties conjugated thereto, wherein the plurality of galactose moieties are disposed at the surface of the matrix core; (ii) a chemiluminescent sensor that in the presence of hydrogen peroxide provides a chemical source of energy capable of inducing a detectable signal from a dye; and (iii) a fluorescent sensor that is decomposed when in the presence of a reactive oxygen or nitrogen species; (b) irradiating the human or non-human subject with an excitation light at a wavelength selected as inducing a fluorescent emission by the fluorescent superconducting polymer; (c) determining the intensities of a first detectable signal at a first wavelength and a second detectable signal at a second wavelength emitted by the fluorescent sensor, wherein the ratio of said intensities, when differing from the ratio obtained from the bifunctional nanoprobe before delivering to the human or non-human subject, indicates an hepatic injury in the subject that generates a reactive nitrogen species; and (d) determining the intensity of a detectable signal emitted from the chemiluminescent sensor, wherein the emission of said detectable signal indicates an hepatic injury in the subject that generates a reactive oxygen species.

In embodiments of this aspect of the disclosure, the intensities of the detectable signals emitted from the fluorescent sensor and the chemiluminescent sensor can be converted to an image overlay of the body of the human or non-human subject, thereby locating a site of hepatic injury in said subject.

In embodiments of this aspect of the disclosure, the method can further comprise the steps of: (1) administering to the human or non-human subject a dose of a compound, wherein the compound is a therapeutic agent, a candidate therapeutic agent, or a compound suspected of having a hepatotoxic effect on the liver of the recipient subject; and (2) repeating steps (a)-(d), whereby the detection of an hepatic injury in the subject that generates a reactive oxygen and/or nitrogen species indicates that the compound has an hepatotoxic effect on the liver of the human or non-human subject.

Yet another aspect of the disclosure encompasses embodiments of a method for determining if a compound is hepatotoxic, said method comprising the steps of: (a) delivering to the liver of to a human or non-human subject a pharmaceutically acceptable composition comprising a bifunctional nanoprobe for detecting hepatic injury and a pharmaceutically acceptable carrier, said nanoprobe comprising: (i) a matrix core comprising: (a) a fluorescent superconducting polymer, wherein the fluorescent superconducting polymer is poly[2,7-(9,9-di-octyl-fluorene)-alt-4,7-bis(thiophen-2-yl)benzo-2,1,3-thiadiazole]; and (b) a copolymer having a plurality of galactose moieties conjugated thereto, wherein the copolymer is comprised of polystyrene and polyethylene glycol monomers, and wherein the plurality of galactose moieties are conjugated to the polyethylene glycol so as to dispose the plurality of galactose moieties at the surface of the matrix core; (ii) a chemiluminescent sensor that in the presence of hydrogen peroxide provides a chemical source of energy capable of inducing a detectable signal from a dye, wherein the chemiluminescent sensor is bis-(2,4,5-trichloro-6-(pentyloxycarbonyl)phenyl)oxalate (CPPO); and (iii) a fluorescent sensor that is decomposed when in the presence of a reactive oxygen or nitrogen species, wherein the fluorescent sensor is 2-[4'-(β-carboxyethylthio)-7'-(1",3",3"-trimethylindolenine)-3',5'-trimethyleneheptatrien-1-yl]-1,3,3-trimethylindolenium perchlorate (IR775S); (b) irradiating the recipient human or non-human subject with an excitation light at a wavelength selected as inducing a fluorescent emission by the fluorescent superconducting polymer; (c) determining the intensities of a first detectable signal at a first wavelength and a second detectable signal at a second wavelength emitted by the fluorescent sensor, wherein the ratio of said intensities, when differing from the ratio obtained from the bifunctional nanoprobe before delivering to the human or non-human subject, indicates an hepatic injury in the subject that generates a reactive nitrogen species; and (d) determining the intensity of a detectable signal emitted from the chemiluminescent sensor, wherein the emission of said detectable signal indicates an hepatic injury in the subject that generates a reactive oxygen species; (e) administering to the human or non-human subject a dose of a compound, wherein the compound is a therapeutic agent, a candidate therapeutic agent, or a compound suspected of having a hepatotoxic effect on the liver of the recipient subject; and (f) repeating steps (a)-(d), whereby the detection of an hepatic injury in the subject that generates a reactive oxygen and/or nitrogen species indicates that the compound has an hepatotoxic effect on the liver of the human or non-human subject.

In embodiments of this aspect of the disclosure, the intensities of the detectable signals emitted from the fluorescent sensor and the chemiluminescent sensor are converted to an image overlay of the body of the human or non-human subject, thereby locating a site of hepatic injury in said subject.

BRIEF DESCRIPTION OF THE DRAWINGS

Many aspects of the disclosure can be better understood with reference to the following drawings.

FIGS. 1A-1G illustrate the composition, mechanism of sensing, and physical characterization of CF-SPN.

FIG. 1A illustrates the molecular structure of the $H_2O_2$-specific chemiluminescent substrate CPPO that serves as a CRET energy donor FIG. 1B illustrates the molecular structure of a PEG-grafted PS copolymer conjugated to galactose for hepatocyte targeting.

FIG. 1C illustrates the molecular structure of the FRET acceptor IR775S that degrades after oxidation by ONOO or HOCl.

FIG. 1D illustrates molecular structure of the NIR fluorescent semiconducting polymer PFODBT, which serves as the CRET energy acceptor and the FRET energy donor.

FIG. 1E illustrates the hydrodynamic diameter distribution of CF-SPN as determined by dynamic light scattering.

FIG. 1F illustrates a transmission electron micrograph of CF-SPN (scale bar=50 nm).

FIG. 1G illustrates the mechanism of simultaneous and discriminate reporting of the generation of ONOO/HOCl and $H_2O_2$ by CF-SPN following drug challenge to the liver and the emission states for each of the chemiluminescent and fluorescent channels at safe drug doses (left) and at toxic drug doses (right).

FIG. 2A illustrates the UV/Vis absorption spectrum of CF-SPN, with a PFODBT maximum at 580 nm and NIR775S maximum at 775 nm.

FIG. 2B illustrates the fluorescence and chemiluminescence spectra of CF-SPN, indicating PFODBT and NIR775S emission maxima at 680 nm and 820 nm, respectively. Chemiluminescence was induced by the addition of 2 μM $H_2O_2$.

FIG. 2C illustrates the specificity of the oxidative degradation of NIR775S encapsulated in CF-SPN (1 μg/mL) determined after 5 min incubation in the presence of 6 μM of the indicated ROS or RNS.

FIG. 2D illustrates the sensitivity and range of fluorescence ratiometric detection of ONOO with CF-SPN (1 μg/mL) following 1 μM incremental additions of NaONOO.

FIG. 2E illustrates the specificity of the chemiluminescent signal of CF-SPN (5 μg/mL) determined in the presence of 6 μM of ROS or RNS.

FIG. 2F illustrates the chemiluminescent response to 1 μm incremental additions of $H_2O_2$ was determined with CF-SPN (2 μg/mL).

FIG. 3A illustrates representative images of mice receiving, from left to right, 300 mg/kg, 150 mg/kg, 75 mg/kg of APAP, or saline intraperitoneally, followed by 0.8 mg CF-SPN i.v. Threshold toxicity is observed for both the chemiluminescence (top row, shown at 18 min after CF-SPN administration) and the fluorescence percent difference (bottom row, shown at 53 min after CF-SPN administration) channels. The emission intensities of the liver for each of the (FIG. 3B) chemiluminescent or (FIG. 3C) normalized fluorescent percent difference (FL Index) channels are shown over time. The black arrows indicate the respective time points shown in FIG. 3A. Values are the mean±s.d. for n=3 mice.

FIG. 3D illustrates representative immunohistochemistry 45 min after drug administration.

FIG. 3E illustrates representative immunohistochemistry 180 min after drug administration. Both nitrotyrosine (top) and TUNEL (bottom) staining were performed, with white arrowheads representing positive cellular or nuclear staining, respectively. Scale bars represent 10 μm.

FIG. 4A illustrates representative images of mice receiving, from left to right, saline, 300 mg/kg APAP i.p. alone, and 300 mg/kg APAP with 200 mg/kg GSH i.v., 2×100 mg/kg 1-ABT i.p., or 0.2 mg/kg t-1,2-DCE i.p., followed by 0.8 mg CF-SPN i.v. Hepatotoxicity was observed to decrease for both the chemiluminescence (top row, shown at 18 min after CF-SPN administration) and the fluorescence index (bottom row, shown at 53 min after CF-SPN administration) channels following scavenger or inhibitor therapy.

FIG. 4B illustrates a cartoon of the mechanism of APAP-induced toxicity, with the effects of bioinactivation by GSH, 1-ABT, and t-1,2-DCE presented. ⊢ indicates inhibition.

FIG. 4C is a graph illustrating the emission intensities of the liver for each of the chemiluminescent ratiometric channels shown over time. The black arrow indicates the respective time points shown in FIG. 4A. Values are the mean±s.d. for n=3 mice.

FIG. 4D is a graph illustrating the emission intensities of the liver for each of the fluorescent ratiometric channels are shown over time. The black arrow indicates the respective time points shown in FIG. 4A. Values are the mean±s.d. for n=3 mice.

FIG. 5A illustrates representative images of mice receiving, from left to right, 200 mg/kg, 100 mg/kg, 50 mg/kg INH, or saline i.p., followed by 0.8 mg CF-SPN i.v. Dose-dependent toxicity is observed for both the chemiluminescence (top row, shown at 10 min after CF-SPN administration) and the fluorescence index (bottom row, shown at 70 min after CF-SPN administration) channels.

FIG. 5B illustrates the emission intensities of the liver for each of the chemiluminescent ratiometric channels shown over time. The black arrow indicates the respective time points shown in FIG. 5A. Values are the mean±s.d. for n=3 mice.

FIG. 5C illustrates the emission intensities of the liver for each of the fluorescent ratiometric channels shown over time. The black arrow indicates the respective time points shown in FIG. 5A. Values are the mean±s.d. for n=3 mice.

FIG. 5D illustrates representative histology (H&E) with corresponding enlargement shown 180 min after drug administration. Increasing degrees of hepatocyte degradation corresponds with increased chemiluminescence and fluorescence signals. Scale bars represent (top) 10 μm and (bottom enlargement) 2.5 μm, respectively.

FIGS. 7A-7C illustrate signal stability and imaging depth penetration for CF-SPN in vitro. FIG. 7A is a graph illustrating the kinetics of chemiluminescent signal production from CF-SPN (5 μg/mL) in 1×PBS incubated with $H_2O_2$ (6 μM).

FIG. 7B is a graph illustrating the stability of the baseline fluorescence ratio and chemiluminescence upon incubation of CF-SPN (5 μg/mL) in undiluted mouse serum at 37° C.

FIG. 7C is a graph illustrating the chemiluminescence imaging depth of penetration of CF-SPN (5 μg/mL) through a gelatin-hemoglobin-intralipid imaging phantom.

FIGS. 8A and 8B illustrate effective liver targeting through the conjugation of galactose to the SPN surface. Nanoparticles composed of PFODBT and PS-g-PEG-Galactose (Gal-SPN) or PS-g-PEG (PEG-SPN) were administered i.v. (0.8 mg). Tissues were excised and imaged 45 min after nanoparticle administration.

FIG. 8A illustrates a representative image of the biodistribution of Gal-SPN (top) and PEG-SPN (bottom).

FIG. 8B illustrates organ fluorescence (ex/em=580/680 nm) quantified and represented as the mean±s.d. (n=3). *p<0.05.

FIG. 9A is a graph showing the chemiluminescent signal from CF-SPN or luminol with or without APAP treatment.

FIG. 9B is a graph illustrating the rescaled y-axis of FIG. 9A showing the lack of any signal generation from luminol.

Figure 1A:
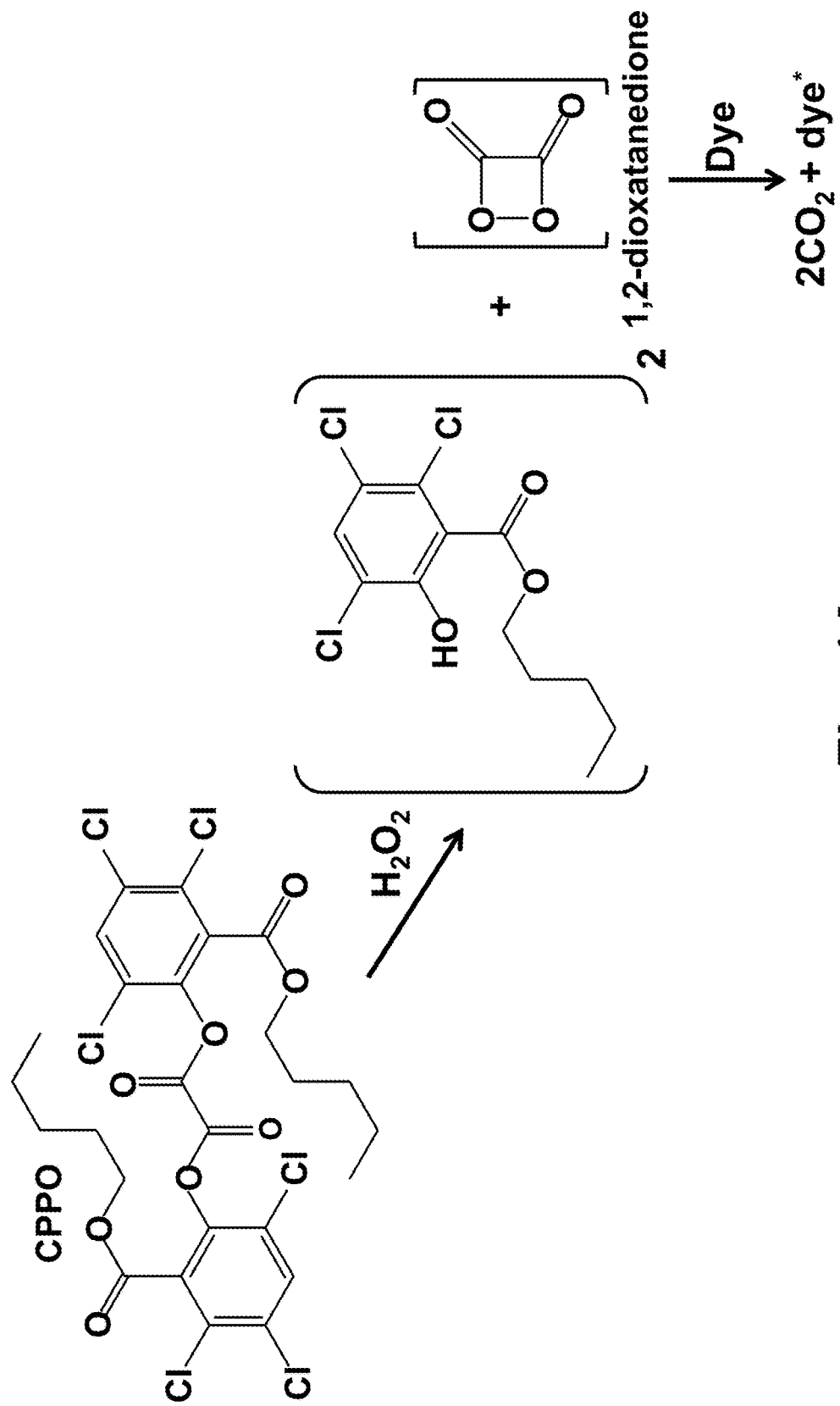
Figure 1B:
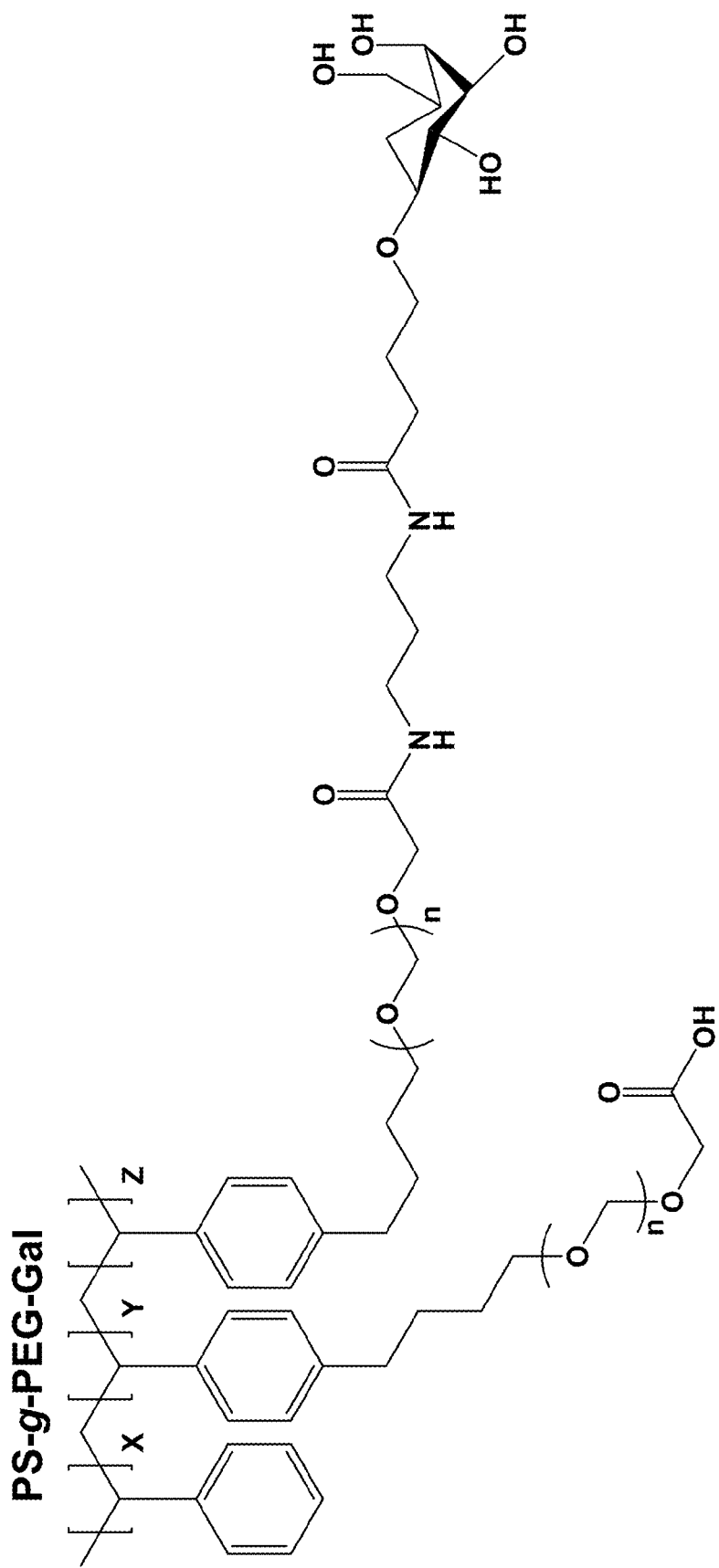

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

The term "pharmaceutically acceptable carrier" as used herein refers to a diluent, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio The term "reactive oxygen and nitrogen species (RONS)" as used herein refers to an oxygen- or nitrogen-containing molecules that are capable of producing oxidative damage to other molecules. Many, but not all, RONS are free radicals. A radical is a group of atoms which behaves as a unit and has one or more unpaired electrons. Examples include, but are not limited to: $H_2O_2$ (hydrogen peroxide), $*O_2^-$ (superoxide radical), *OH, (hydroxyl radical), $ONOO^-$ (peroxynitrite), $O_2^1$ (singlet oxygen), $O^3$ (ozone), *NO (nitric oxide), and $*NO_2$ (nitrogen dioxide).

The term "nanoparticle" as used herein refers to a particle having a diameter of between about 1 and about 1000 nm. Similarly, by the term "nanoparticles" is meant a plurality of particles having an average diameter of between about 1 and about 1000 nm.

The terms "core" or "nanoparticle core" as used herein refers to the inner portion of nanoparticle. A core can substantially include a single homogeneous monoatomic or polyatomic material. A core can be crystalline, polycrystalline, or amorphous. A core may be "defect" free or contain a range of defect densities. In this case, "defect" can refer to any crystal stacking error, vacancy, insertion, or impurity entity (e.g., a dopant) placed within the material forming the core. Impurities can be atomic or molecular.

In particular, it is understood that the nanoparticle core of the compositions of the disclosure can comprise a superconducting polymer that may emit a fluorescent light when irradiated by suitable incident energy. The superconducting polymers suitable for use in the compositions of the disclosure may include, but are not limited to, such as: (a) polyfluorene (PF) derivatives including, but not limited to: poly[(9,9-dioctyl-2,7-divinylenefluorenylene)-alt-co-{2-methoxy-5-(2-ethylhexyloxy)-1,4-phenylene}], poly[2,7-(9,9-di-octyl-fluorene)-alt-4,7-bis(thiophen-2-yl)benzo-2,1,3-thiadiazole], poly[(9,9-dioctyl-2,7-divinylenefluorenylene)-alt-co-(9,10-anthracene)], poly[{9,9-dihexyl-2,7-bis(1-cyanovinylene)fluorenylene}-alt-co-{2,5-bis(N,N'-diphenylamino)-1,4-phenylene}], poly[(9,9-dioctylfluorenyl-2,7-diyl)-alt-(benzo[2,1,3]thiadiazol-4,7-diyl)], poly[2,7-(9,9-di-octyl-fluorene)-alt-4,7-bis(thiophen-2-yl)benzo-2,1,3-thiadiazole], poly[(9,9-dioctylfluorenyl-2,7-diyl)-co-(1,4-diphenylene-vinyl-ene-2-methoxy-5-{2-ethylhexyloxy}-benzene)]; poly[(9,9-dioctyl-2,7-divinylenefluorenylene)-alt-co-(1,4-phenylene)], poly[(9,9-dioctylfluorenyl-2,7-diyl)-co-(N,N'-diphenyl)-N,N'-di(p-butylphenyl)-1,4-diamino-benzene)], poly[(9,9-dihexylfluorenyl-2,7-diyl)-co-(9,10-anthracene)], poly[(9,9-dioctylfluorenyl-2,7-diyl)-alt-co-(N,N'-bis{4-butyl-phenyl}-benzidineN,N'-{1,4-diphenylene})], poly[(9,9-dihexylfluorenyl-2,7-diyl)-alt-co-(2-methoxy-5-{2-ethylhexyloxy}-1,4-phenylene)], poly[(9,9-dihexylfluorenyl-2,7-diyl)-alt-co-(9,9'-spiro-bifluorene-2,7-diyl)], poly[(9,9-dihexylfluorenyl-2,7-diyl)-alt-co-(bithiophene)], poly[(9,9-dihexylfluorenyl-2,7-diyl)-alt-co-(bithiophene)], and poly[(9,9-dioctylfluorenyl-2,7-diyl)-co-(4,4'-(N-(p-butyl-phenyl))diphenylamine)]; (b) Poly(p-phenylene vinylene) (PPV) derivatives including, but not limited to: poly[2-methoxy-5-(2-ethylhexyloxy)-1,4-phenylenevinylene] (MEH-PPV), poly{[2-[2',5'-bis(2''-ethylhexyloxy)phenyl]-1,4-phenylenevinylene]-co-[2-methoxy-5-(2'-ethylhexyloxy)-1,4-phenylenevinylene]}, poly[2-methoxy-5-(2-ethylhexyloxy)-1,4-(1-cyanovinylene-1,4-phenylene)], and poly[{2-methoxy-5-(2-ethylhexyloxy)-1,4-(1-cyanovinylenephenyl-ene)}-co-{2,5-bis(N,N'-diphenylamino)-1,4-phenylene}]); and (c) Polythiophene (PT) derivatives including but not limited to: poly[2,6-(4,4'-bis(2-ethylhexyl)dithieno[3,2-b:2',3'-d]siloleyalt-4,7(2,1,3-benzothiadiazole)], poly[N-9'-heptadecanyl-2,7-carbazole-alt-5,5-(4',7'-di-2-thienyl-2',1',3'-benzothiadiazole)], poly[3-hexylthiophene-2,5-diyl], poly[2,5-bis(3-dodecylthiophen-2-yl)thieno[3,2-b]thiophene], poly[3-decylthiophene-2,5-diyl], poly[3-methyl-4-decylthiophene-2,5-diyl], poly[3-methyl-4-octylthiophene-2,5-diyl], poly[3-methyl-4-hexylthiophene-2,5-diyl], poly[3-methyl-4-butylthiophene-2,5-diyl], poly[3-decylthiophene-2,5-diyl], and poly[3-octylthiophene-2,5-diyl], poly[3-butylthiophene-2,5-diyl].

Nanoparticles of the disclosure may further comprise a "coat" or "shell" of a second material that surrounds the core. A coat can include a layer of material, either organic or inorganic, that covers or substantially covers the surface of the core of a nanoparticle. A coat may be crystalline, polycrystalline, or amorphous or may comprise, for example, hydrophilic regions of a molecule where hydrophobic regions thereof are either conjugated to are integral to the underlying nanoparticle core.

A coat or shell may be "complete", indicating that the coat substantially or completely surrounds the outer surface of the core (e.g., substantially all surface atoms of the core are covered with coat material). Alternatively, the coat may be "incomplete" such that the coat partially surrounds the outer surface of the core (e.g., partial coverage of the surface core atoms is achieved). In addition, it is possible to create coats of a variety of thicknesses, which can be defined in terms of the number of "monolayers" of coat material that are bound to each core. A "monolayer" is a term known in the art referring to a single complete coating of a material (with no additional material added beyond complete coverage). Incomplete monolayers may be either homogeneous or inhomogeneous, forming islands or clumps of coat material on the surface of the nanoparticle core. Coats may be either uniform or non-uniform in thickness. In the case of a coat having non-uniform thickness, it is possible to have an "incomplete coat" that contains more than one monolayer of coat material. A coat may optionally comprise multiple layers of a plurality of materials in an onion-like structure, such that each material acts as a coat for the next-most inner layer. Between each layer there is optionally an interface region. The term "coat" as used herein describes coats formed from substantially one material as well as a plurality of materials that can, for example, be arranged as multi-layer coats.

It will be understood by one of ordinary skill in the art that when referring to a population of nanoparticles as being of a particular "size", what is meant is that the population is made up of a distribution of sizes around the stated "size". Unless otherwise stated, the "size" used to describe a particular population of nanoparticles will be the mode of the size distribution (i.e., the peak size). By reference to the "size" of a nanoparticle is meant the length of the largest straight dimension of the nanoparticle. For example, the size of a perfectly spherical nanoparticle is its diameter.

The term "polymer" as used herein refers to molecules comprising two or more monomer subunits that may be identical repeating subunits or different repeating subunits. A monomer generally comprises a simple structure, low-molecular weight molecule containing carbon. Polymers may optionally be substituted. Polymers that can be used in the present disclosure include without limitation vinyl, acryl, styrene, carbohydrate derived polymers, polyethylene glycol (PEG), polyoxyethylene, polymethylene glycol, poly-trimethylene glycols, polyvinylpyrrolidone, polyoxyethylene, polyoxypropylene block polymers, and copolymers, salts, and derivatives thereof. In aspects of the disclosure, the polymer is poly(2-acrylamido-2-methyl-1-propanesulfonic acid); poly(2-acrylamido-2-methyl,-1-propanesulfonic acid-coacrylonitrile, poly(2-acrylamido-2-methyl,-1-propanesulfonic acid-co-styrene), poly(vinylsulfonic acid); poly(sodium 4-styrenesulfonic acid); and sulfates and sulfonates derived therefrom; poly(acrylic acid), poly(methylacrylate), poly(methyl methacrylate), and polyvinyl alcohol).

The term "FRET" as used herein refers to fluorescence resonance energy transfer between molecules. In FRET methods, one fluorophore is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g., on the same, or a neighboring molecule). FRET techniques are well known in the art, and can be readily used to detect the titanium oxide-bound peptides of the present disclosure. See for example U.S. Pat. Nos. 5,668,648, 5,707,804, 5,728,528, 5,853,992, and 5,869,255 (for a description of FRET dyes), T Mergny et al., (1994) Nucleic Acid Res. 22:920-928, and Wolf et al., (1988) Proc. Natl. Acad. Sci. USA 85:8790-8794 (for general descriptions and methods for FRET), each of which is hereby incorporated by reference in its entirety.

The term "fluorescence" as used herein refers to a luminescence that is mostly found as an optical phenomenon in cold bodies, in which the molecular absorption of a photon triggers the emission of a photon with a longer (less energetic) wavelength. The energy difference between the absorbed and emitted photons ends up as molecular rotations, vibrations or heat. Sometimes the absorbed photon is in the ultraviolet range, and the emitted light is in the visible range, but this depends on the absorbance curve and Stokes shift of the particular fluorophore.

The term "fluorophore" as used herein refers to a component of a molecule that causes a molecule to be fluorescent. It is a functional group in a molecule which will absorb energy of a specific wavelength and re-emit energy at a different (but equally specific) wavelength. The amount and wavelength of the emitted energy depend on both the fluorophore and the chemical environment of the fluorophore. Fluorophores for use in the compositions of the disclosure include, but are not limited to, fluorescein isothiocyanate (FITC), a reactive derivative of fluorescein, which has been one of the most common fluorophores chemically attached to other, non-fluorescent, molecules to create new fluorescent molecules for a variety of applications. Other historically common fluorophores are derivatives of rhodamine (TRITC), coumarin, and cyanine. Newer generations of fluorophores such as the ALEXA FLUORS® and the DYLIGHT FLUORS® are generally more photostable, brighter, and less pH-sensitive than other standard dyes of comparable excitation and emission.

The term "fluorescent sensor" as used herein refers to a fluorophore that is decomposed to a non-fluorescent moiety when contacted by a reactive oxygen or nitrogen species.

The term "chemiluminescent sensor" as used herein refers to a compound that in the presence of hydrogen peroxide provides a chemical source of energy capable of inducing a detectable signal from a dye.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores (chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.,), HILYTE® Fluors (AnaSpec), and DYLITE® Fluors (Pierce, Inc.).

The term "fluorescent acceptor molecule" as used herein refers to any molecule that can accept energy emitted as a result of the activity of a bioluminescent donor protein, and re-emit it as light energy.

By the term "detectable signal emitter" is meant, for the purposes of the specification or claims, a label molecule that is incorporated indirectly or directly into a nanoparticle, wherein the label molecule facilitates the detection of the nanoparticle in which it is incorporated, for example when the nanoparticle of the disclosure is at a site of inflammation and activated by interaction between the nanoparticle or the quencher component thereof and a RONS. Thus, "detectable signal emitter" is used synonymously with "label molecule".

The term "$NH_2$-functionalized conjugated polymer" as used herein refers to a nanoparticle formed by co-condensing one or more types of monomer to form a polymer and wherein on the outer surface of said nanoparticle are located amine groups that are available for conjugating with another molecular entity that may have such as a reactive carboxyl group thereon.

The term "image overlay" as used herein refers to where one image, which may be a color image derived from a luminescent or fluorescent label, is superimposed on a gray-scale photographic image of the object (e.g., a small animal) using overlay and image analysis software. Usually a region of interest is manually selected over an area of signal intensity, and the maximum or average intensity is recorded as "photons sec$^{-1}$ cm$^{-2}$ squared steradian$^{-1}$ (a steradian is a unit of solid angle). When the exposure conditions (including time, F/STOP, height of sample shelf, binning ratio, and time after injection with optical substrate) are kept substantially identical, the measurements are highly reproducible The terms "subject" and "patient" as used herein refer to humans and on-human animals such as mammals (e.g., cats, dogs, horses, etc.), living cells, and other living organisms. A living organism can be as simple as, for example, a single eukaryotic cell or as complex as a mammal. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. In some embodiments, a system includes a sample and a subject.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Abbreviations

CPN, conjugated polymer nanoparticle; CRET-FRET-superconducting polymer nanoparticle(s); RONS, reactive oxygen and/or nitrogen species; RNS, reactive nitrogen species; ROS, reactive oxygen species; FRET, fluorescence resonance energy transfer; CRET, chemiluminescence energy transfer; PFODBT, poly[2,7-(9,9-dioctylfluorene)-alt-4,7-bis(thiophen-2-yl)benzo-2,1,3-thiadiazole]; CPPO, bis-(2,4,5-trichloro-6-(pentyloxycarbonyl)phenyl)oxalate; PEG, polyethylene glycol; APAP, anti-pyretic acetaminophen; NAPQI, N-acetylparaquinonimine; 1-ABT, 1-aminobenzotriazole; t-1,2-DCE, trans-1,2-dichloroethylene; INH, isoniazid; i.p. intraperitoneally;

Description

Within the liver, drugs undergo enzymatic biotransformation to increase metabolite hydrophilicity and enhance clearance from the body (Srivastava et al., (2010) *Handbook Exp. Pharmacol.* pp 165-194; Park et al., (2005) *Ann. Rev. Pharmacol. Toxicol.* 45: 177-202; Holt & Ju (2010) *Handbook Exp. Pharmacol.* pp 3-27; Walsh & Miwa (2011) *Ann. Rev. Pharmacol. Toxicol.* 51: 145-167). Biotransformation can, however, result in drug bioactivation to highly unstable reactive metabolites through one- or two-electron oxidation reactions that form reactive radicals or electrophiles, respectively (Walsh & Miwa (2011) *Ann. Rev. Pharmacol. Toxicol.* 51: 145-167). It is well accepted that, in designing drug candidates, bioactivation should be avoided, as reactive metabolite formation is a necessary initiating step underlying the majority of drug-induced hepatotoxicity (Srivastava et al., (2010) *Handbook Exp. Pharmacol.* pp 165-194; Reese et al. (2011) *Chem. Biol. Interact.* 192: 60-64; Antoine et al., (2008) *Expert Opin. Drug Metab. Toxicol.* 4: 1415-1427; Tang & Lu (2010) *Drug Metab. Rev.* 42: 225-249; Thompson et al., (2011) *Chem. Biol. Interact.* 192: 65-71).

Reactive metabolites are short-lived with half-lives of less than one second, precluding their detection in plasma and necessitating in situ detection at their sites of formation (Srivastava et al., (2010) *Handbook Exp. Pharmacol.* pp 165-194; Park et al., (2005) *Ann. Rev. Pharmacol. Toxicol.* 45: 177-202). Even though electrophilic reactive metabolites have historically been the focus of drug hepatotoxicity prediction due to the ease of detecting their covalent binding to endogenous nucleophiles (i.e. protein, glutathione) (Srivastava et al., (2010) *Handbook Exp. Pharmacol.* pp 165-194; Walsh & Miwa (2011) *Ann. Rev. Pharmacol. Toxicol.* 51: 145-167) they are a poor predictor of the hepatotoxic potential of the parent drug molecule (Srivastava et al., (2010) *Handbook Exp. Pharmacol.* pp 165-194; Thompson et al., (2011) *Chem. Biol. Interact.* 192: 65-71) and fail to represent a mechanistic link between the administered drug and toxic outcome (Willmann et al., (2008) *Nat. Rev. Drug Discov.* 7: 591-607; Tengowski & Kotyk (2005) *Prog. Drug. Res.* 62: 257-278; Wang & Yan (2008) *Lab Anim.* 42: 433-441; Antoine et al., (2008) *Expert Opin. Drug Metab. Toxicol.* 4: 1415-1427; Walsh & Miwa (2011) *Ann. Rev. Pharmacol. Toxicol.* 51: 145-167).

Radical species, specifically reactive oxygen species (ROS) or reactive nitrogen species (RNS), are proposed to play a central role in drug-induced hepatotoxicity and to be an early unifying event linking the bioactivation of the majority of drugs to liver cell death and hepatotoxicity (Antoine et al., (2008) *Expert Opin. Drug Metab. Toxicol.* 4: 1415-1427; Russmann et al., (2009) *Curr. Med. Chem.* 16: 3041-3053; Pessayre et al., *Handbook Exp. Pharmacol.* pp 311-365; Deavall et al., (2012) *J. Toxicol.* 2012: 645460). Therefore, the unifying link between ROS and RNS production and hepatotoxicity argues for their use as an alternative safety biomarker to covalent binding (Russmann et al., (2009) *Curr. Med. Chem.* 16: 3041-3053; Walsh & Miwa (2011) *Ann. Rev. Pharmacol. Toxicol.* 51: 145-167; Pessayre et al., *Handbook Exp. Pharmacol.* pp 311-365).

ROS, including hydrogen peroxide ($H_2O_2$), can be generated directly by oxidative Phase I enzymes (e.g. cytochrome P450, peroxidase) during metabolism, or indirectly by the reaction of radical drug metabolites with oxygen (Walsh & Miwa (2011) *Ann. Rev. Pharmacol. Toxicol.* 51: 145-167). RNS, on the other hand, such as peroxynitrite ($ONOO^-$), are the result of drug metabolite-induced mitochondrial toxicity mediated through disruption of the electron transport chain (Walsh & Miwa (2011) *Ann. Rev. Pharmacol. Toxicol.* 51: 145-167; Pessayre et al., *Handbook Exp. Pharmacol.* pp 311-365; Deavall et al., (2012) *J. Toxicol.* 2012: 645460). As a result of their distinct sources of production, the simultaneous and differential detection of ROS and RNS are useful for providing additional insight into the mechanism of drug-induced hepatotoxicity in vivo.

The technical challenge of detecting these radical species, even individually, has previously prevented their implementation for pre-clinical drug safety screening (Sakatis et al., (2012) *Chem. Res. Toxicol.* 25: 2067-2082; Walsh & Miwa (2011) *Ann. Rev. Pharmacol. Toxicol.* 51: 145-167). However, the present disclosure encompasses compositions and methods of use thereof that, through the union of optical molecular imaging techniques with rationally designed liver-targeted nanoparticles, simultaneously capable of activatable fluorescent ratiometric and chemiluminescent imaging, allow in vivo, real-time and differential detection of ONOO and $H_2O_2$ for monitoring drug-induced hepatotoxicity.

Accordingly, the present disclosure encompasses embodiments of activatable nanoprobes especially useful for in vivo longitudinal imaging of drug hepatotoxicity with oxidative and nitrosative stress as the safety biomarkers. Both $H_2O_2$ and $ONOO^-$ are important mediators of radical stress (Walsh & Miwa (2011) *Ann. Rev. Pharmacol. Toxicol.* 51: 145-167) and, therefore, two channels of optical detection, intrinsically free from cross-talk, were engineered into the CPN of the disclosure: (1) chemiluminescence resonance energy transfer (CRET) between the conjugated polymer matrix of the SPNs and an incorporated chemiluminescent substrate, allowing for the luminescent detection of $H_2O_2$ (Lee et al., (2007) *Nat. Mater.* 6: 765-769; Tsunoda & Imai (2005) *Anal. Chim. Acta* 541: 13-23); and (2) fluorescence resonance energy transfer (FRET) between the SPN matrix and an oxidation-degradable fluorophore, permitting fluorescence ratiometric detection of ONOO (Oushiki et al., (2010) *J. Am. Chem. Soc.* 132: 2795-2801).

These novel CRET-FRET-SPN (CF-SPN) nanoprobes of the disclosure have been applied for the real-time in vivo monitoring of hepatotoxicity resulting from challenges with two widely used hepatotoxic drugs: the anti-inflammatory and anti-pyretic acetaminophen (APAP) (McGill & Jaeschke (2013) *Recent Adv. Relation to Hepatotoxicity Diagnosis. Pharm Res.*), and the anti-tuberculosis agent isoniazid (INH) (Holt & Ju (2010) *Handbook Exp. Pharmacol.* pp 3-27). While the mechanism of APAP-induced hepatotoxicity is well established and due mainly to Phase I metabolism, the toxic mechanism of INH is less known, but is attributed mainly to Phase II metabolism (Metushi et al., (2012) *Chem. Res. Toxicol.* 25: 2567-2576).

In addition to the capability of imaging the dose-dependence of oxidative and nitrosative stress, and the effect of enzyme inhibition and radical scavengers on toxicity, the positive detection of radical stress by the CF-SPNs of the disclosure precedes histological changes that are indicative of hepatocyte damage, further reflecting the utility of this novel nanoprobe for the early and longitudinal detection of drug-induced hepatotoxicity in vivo.

Figure 13:
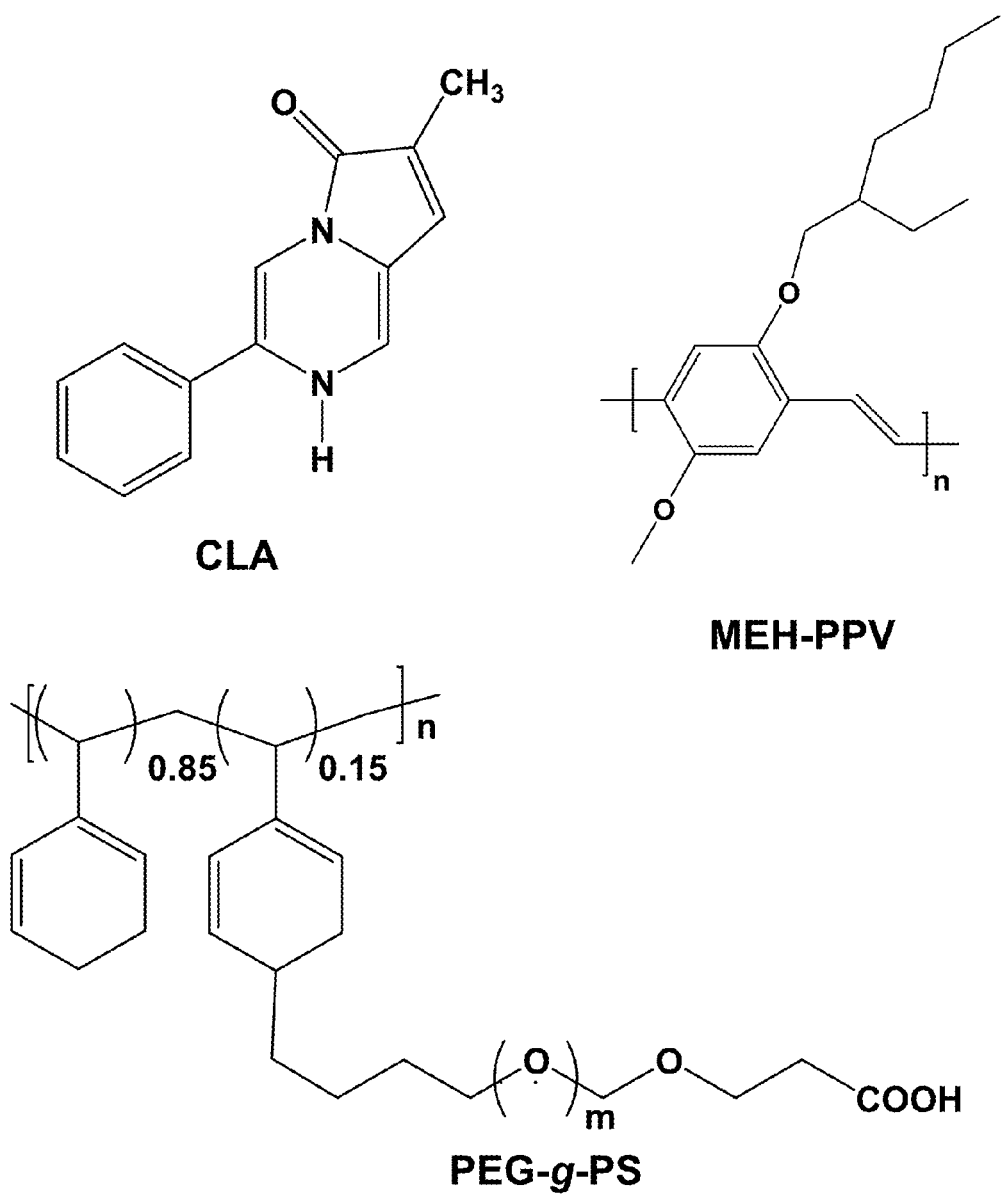
FIG. 13 illustrates the structures of 2-Methyl-6-phenyl-3,7-dihydroimidazo[1,2-a]pyrazin-3-one (CLA); Poly[2-methoxy-5-(2-ethylhexyloxy)-1,4-phenylenevinylene] (MEH-PPV), and PEG-g-PS.

Composition and Sensing Mechanism of CF-SPN:

The CF-SPNs of the disclosure can be comprised of, but are not limited to, four materials optimal for in vivo optical imaging of hepatic radical stress (as shown in FIGS. 1A-1D). In some embodiments of the CF-SPNs, the matrix of the nanoparticle can comprise a near-infrared (NIR) fluorescent semiconducting polymer such as poly[2,7-(9,9-dioctylfluorene)-alt-4,7-bis(thiophen-2-yl)benzo-2,1,3-thiadiazole] (PFODBT), and a galactosylated graft copolymer of polystyrene and polyethylene glycol (PS-g-PEG-Gal). The remaining two components of the CF-SPN form the sensing moieties of the nanoprobe, each differing in analyte sensitivity and in optical output mechanism. In some embodiments the semiconducting polymer may be, but is not limited to, a PPV derivative including but not limited to poly[2-methoxy-5-(2-ethylhexyloxy)-1,4-phenylenevinylene] (MEH-PPV), poly{[2-[2',5'-bis(2"-ethylhexyloxy) phenyl]-1,4-phenylenevinylene]-co-[2-methoxy-5-(2'-ethylhexyloxy)-1,4-phenylenevinylene]}, poly[2-methoxy-5-(2-ethylhexyloxy)-1,4-(1-cyanovinylene-1,4-phenylene)], and poly[{2-methoxy-5-(2-ethylhexyloxy)-1,4-(1-cyanovinylenephenyl-ene)}-co-{2,5-bis(N,N'-diphenylamino)-1,4-phenylene}]). A particularly advantageous PPV derivative is poly[2-methoxy-5-(2-ethylhexyloxy)-1,4-phenylenevinylene] (MEH-PPV) as shown in FIG. 13 that, when combined with a chemiluminescent substrate such as CLA or MCLA (shown in FIG. 13) result in chemiluminescence in the presence of an ROS.

In some embodiments of the disclosure, the fluorescence-based sensor is a cyanine dye, such as diaminocyanine (shown in FIG. 17), 2-[4'-(β-carboxyethylthio)-7'-(1",3",3"-trimethylindolenine)-3',5'-trimethyleneheptatrien-1-yl]-1,3,3-trimethylindolenium perchlorate (IR775S), or the like that irreversibly decomposes in the presence of ONOO and HOCl by the oxidative cleavage of its polymethine linkers (Oushiki et al., (2010) *J. Am. Chem. Soc.* 132: 2795-2801). The chemiluminescence-based sensor can be, for example, a hydrophobic peroxyoxalate such as bis-(2,4,5-trichloro-6-(pentyloxycarbonyl)phenyl)oxalate (CPPO), which rapidly and selectively decomposes in the presence of $H_2O_2$ to form the high energy 1,2-dioxetanedione intermediate known to excite nearby dye molecules to emit light (Lee et al., (2007) *Nat. Mater.* 6: 765-769; Lim et al., (2010) *Adv. Func. Mat.* 20: 2644-2648; Zheng et al., (2012) *Adv. Mater.* 24: OP194-9, OP186).

Figure 18:
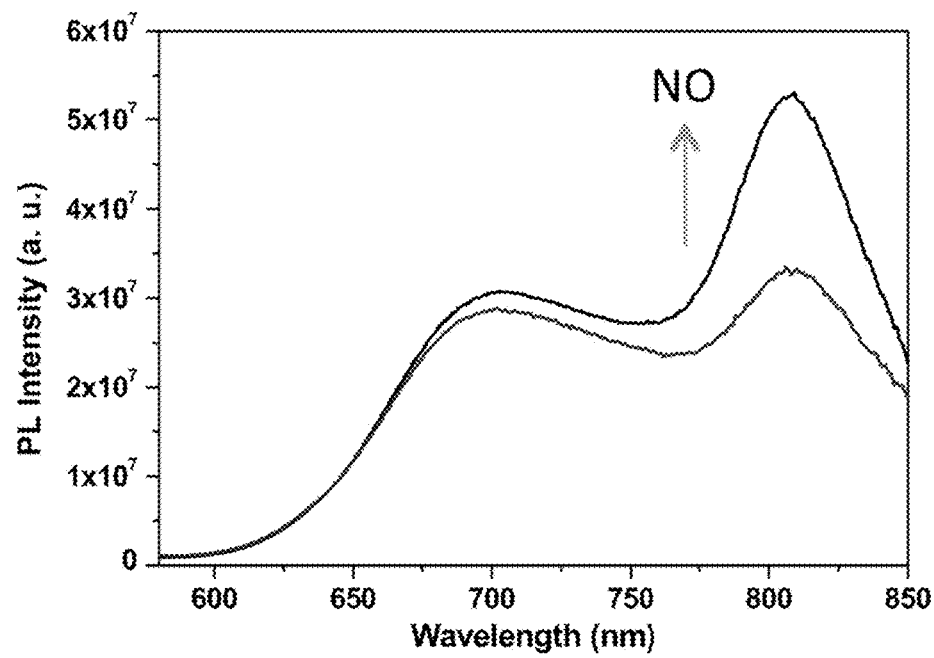
FIG. 18 illustrates the fluorescence spectra of the SPN in the absence and presence of NO.

In some embodiments of the sensors of the disclosure, the semiconducting polymer such as PFODBT may include diaminocyanine or a derivative thereof, thereby obtaining an NO response as shown in FIG. 18.

Accordingly, while IR775S is a fluorescent dye sensitive to ONOO and HOCl, CPPO is a source of chemical energy that, upon decomposition by $H_2O_2$, can induce the emission of local fluorescent dyes in the absence of excitation light source. The four components were formulated into CF-SPN through a nanoprecipitation method resulting in spherical nanoparticles with average diameters of approximately 50 nm as determined by both dynamic light scattering, as shown in FIG. 1E and transmission electron microscopy, as shown in FIG. 1F.

Within the CF-SPN, the preferential hydrophobic interaction of PS with PFODBT drives the presentation of the PEG and conjugated galactose residues on the SPN surface. The surface presentation of galactose is desirable for the specific targeting of the asialoglycoprotein receptor (AS-GPR) on the sinusoidal membrane of hepatocytes, which has been shown to enhance liver uptake of nanoparticles following intravenous administration (Ding et al., (2012) *J. Control Release*; Hu et al., (2013) *ACS Nano*; Zhang et al. (2013) *J. Pharm. Sci.* 102: 145-153). Once in the liver, the CF-SPN of the disclosure simultaneously and selectively detects the formation of both ONOO/HOCl and $H_2O_2$ following drug challenge using fluorescence and chemiluminescence imaging, with the two independent optical imaging channels intrinsically free from cross-talk, as shown in FIG. 1G.

Within each of the optical channels, CF-SPN can exist in one of two states depending on the degree of drug-induced oxidative and nitrosative stress. Thus, within the fluorescent channel (FIG. 1D, top) the state of CF-SPN depends on the degree of FRET that occurs between the PFODBT of the nanoprobe matrix and the encapsulated ONOO/HOCl sensor IR775S. In the absence of these oxidative species, FRET occurs and the CF-SPN emits at both 680 nm and 820 nm following excitation of the PFODBT. However, in the presence of ONOO or HOCl, IR775S is irreversibly degraded, abolishing FRET to result in an emission enhancement at 680 nm solely from PFODBT.

Figures 1C, 1D:
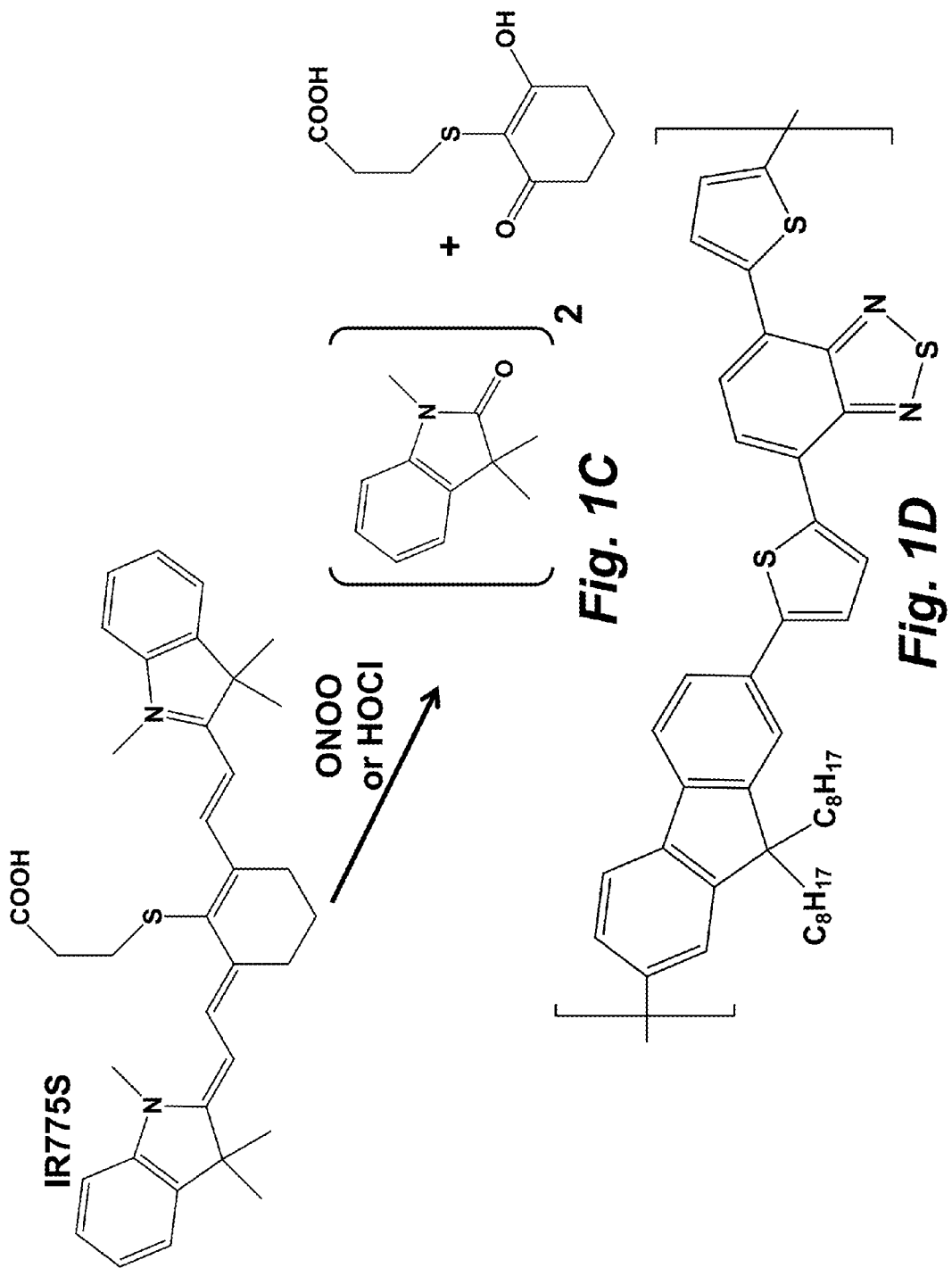
Figure 1G:
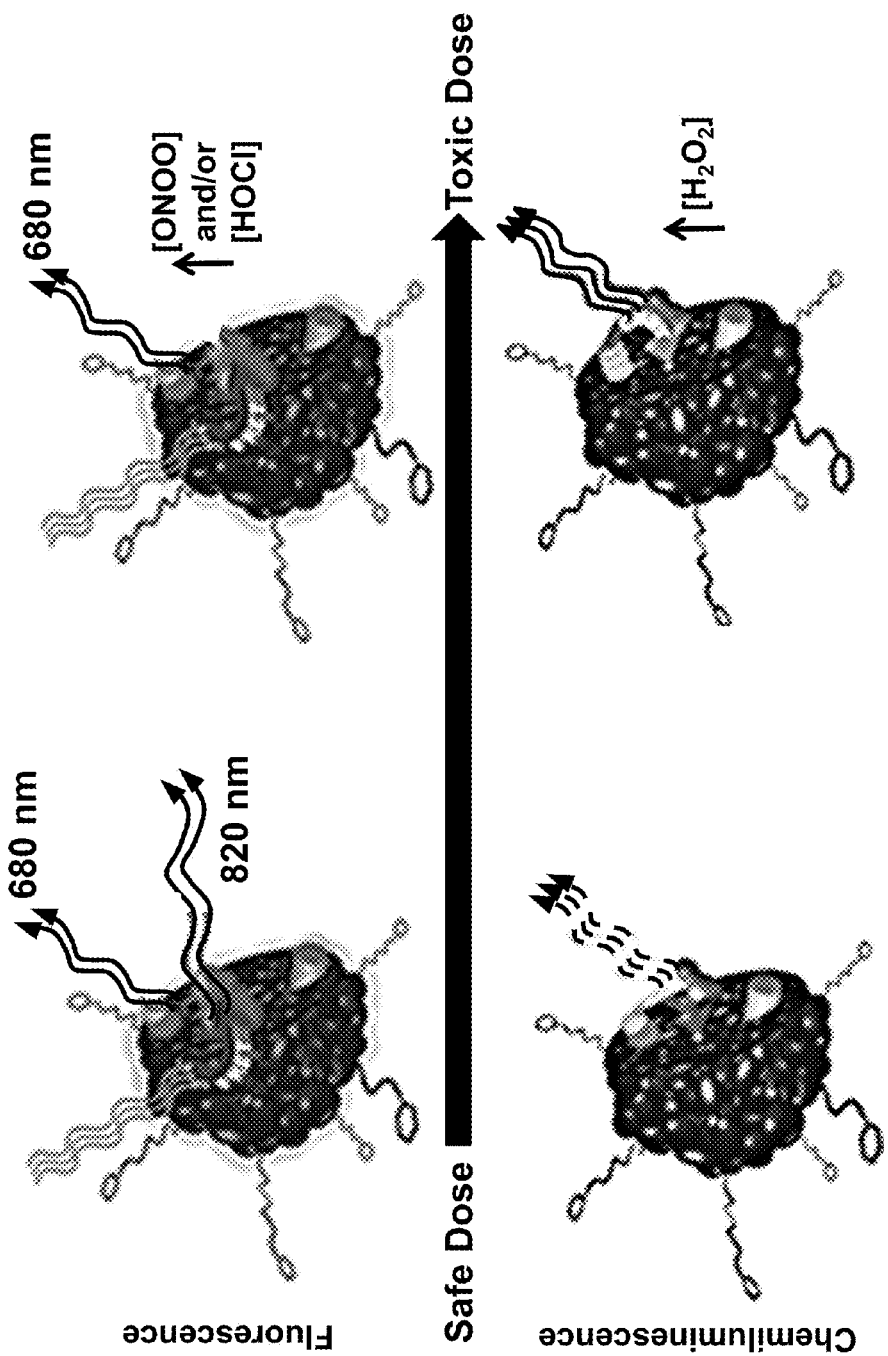

Within the chemiluminescent channel, as shown in FIG. 1D, bottom, the state of CF-SPN depends on the degree of CRET between CPPO, the encapsulated $H_2O_2$-sensitive peroxyoxalate, and PFODBT. Upon elevated local production of $H_2O_2$, the high energy 1,2-dioxatanedione forms from CPPO decomposition, inducing PFODBT luminescence without external excitation. Therefore, through ratiometric fluorescence imaging to monitor the loss of FRET, and through chemiluminescence imaging to monitor the onset of CRET, both nitrosative stress and oxidative stress as causes of drug-induced hepatotoxicity may simultaneously and discriminately be monitored.

Figure 2A:
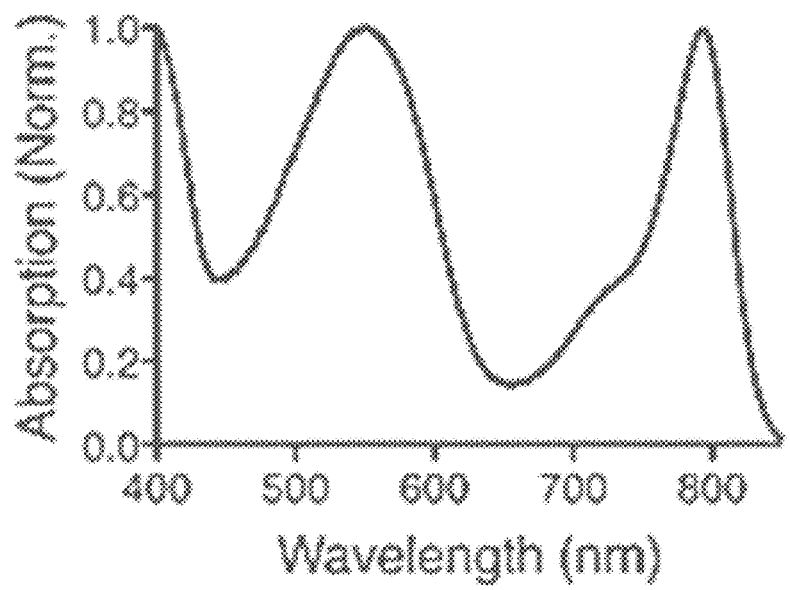
FIGS. 2A-2F illustrate spectral characterization, specificity, and sensitivity of CF-SPN in vitro. All experiments were performed with CF-SPN (1 μg/mL) in 1×PBS unless otherwise stated.
Figure 2B:
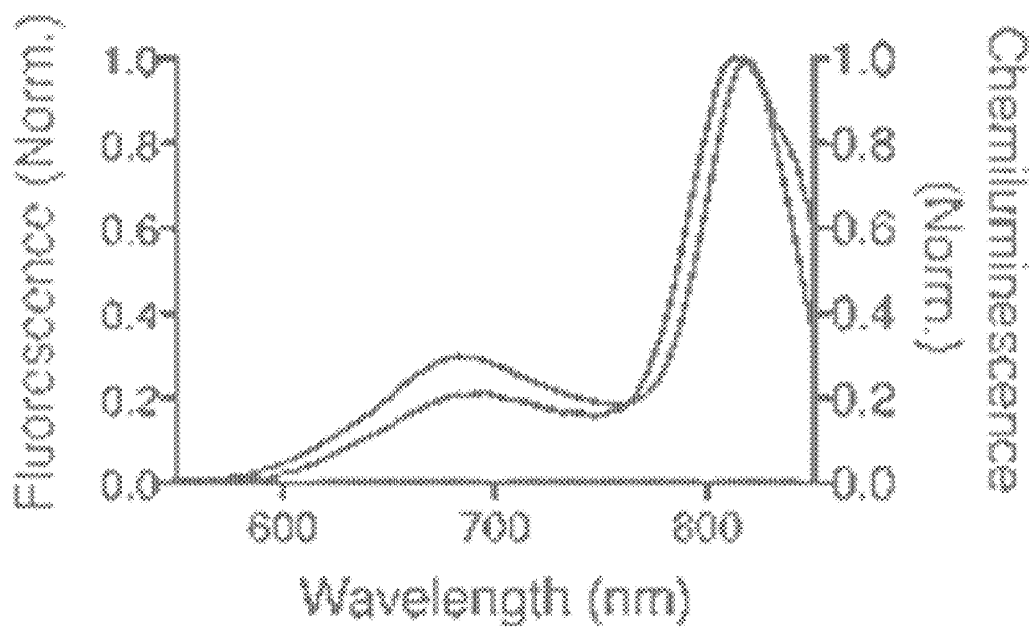

In Vitro Characterization of CF-SPN:

The spectral characteristics of CF-SPN were determined by UV/Vis absorption, as shown in FIG. 2A, and by both fluorescence and chemiluminescence spectroscopy (FIG. 2B). The UV/Vis spectrum demonstrates both the broad absorption of PFODBT (500-600 nm), as well as a peak at 775 nm corresponding to IR775S. Under excitation of CF-SPN at 580 nm, fluorescence from both PFODBT (680 nm) and from IR775S (800 nm) can be observed (FIG. 2B), indicating efficient FRET from the CF-SPN matrix (PFODBT) to the ONOO/OCl sensor dye (IR775S).

Likewise, after addition of $H_2O_2$ without any external light excitation, luminescence from both PFODBT and IR775S was observed (FIG. 2B). This not only confirms the successful encapsulation of the $H_2O_2$-sensitive chemiluminescent energy donor CPPO within CF-SPN, but also demonstrates the efficient CRET from CPPO decomposition to PFODBT and IR775S.

Figure 2C:
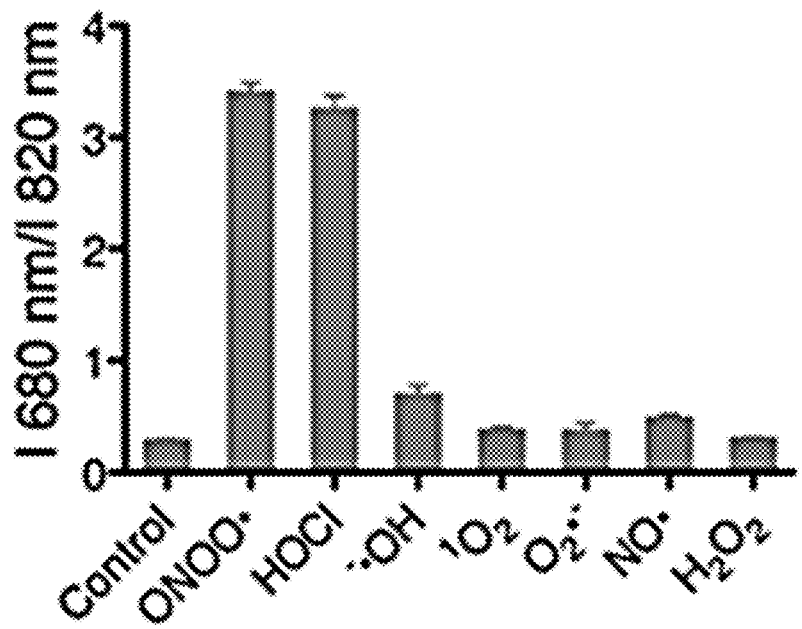
Figure 2D:
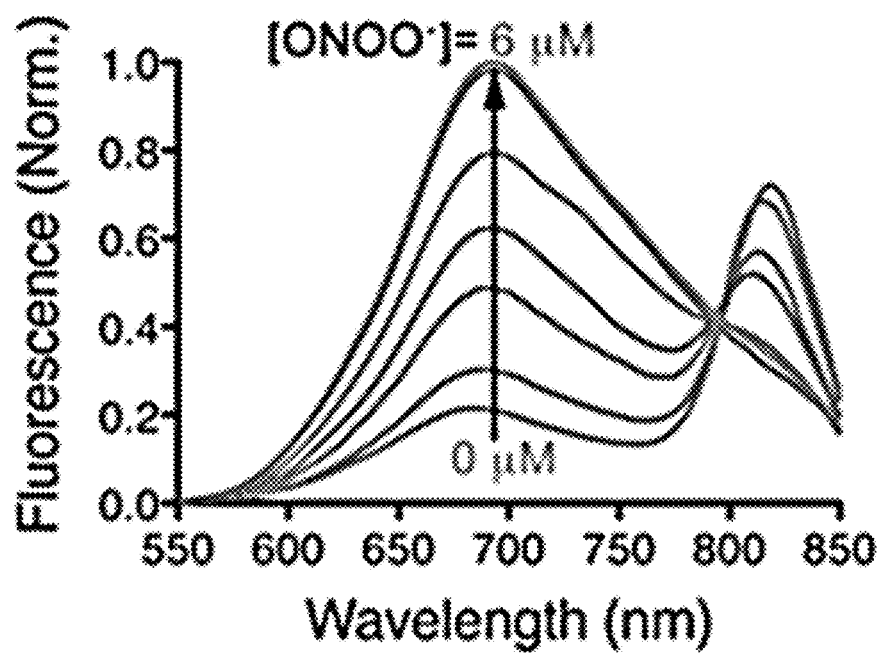

The specificity of CF-SPN towards ROS and RNS has been evaluated under physiological conditions. By monitoring the decrease of emission from the CF-SPN particles at 820 nm following excitation at 580 nm, the loss of FRET-induced emission from IR775S upon its oxidative degradation was quantified (FIG. 2C), indicating that the fluorescent response of CF-SPN was most sensitive to the presence of ONOO and HOCl. As an example of the fluorescence spectral change of CF-SPN in oxidative microenvironments, FIG. 2D shows the progressive loss of emission at 820 nm and concurrent gain in emission at 680 nm with the stepwise addition of ONOO. The fluorescence limit of detection of ONOO and OCl was 10 nM.

Figure 2E:
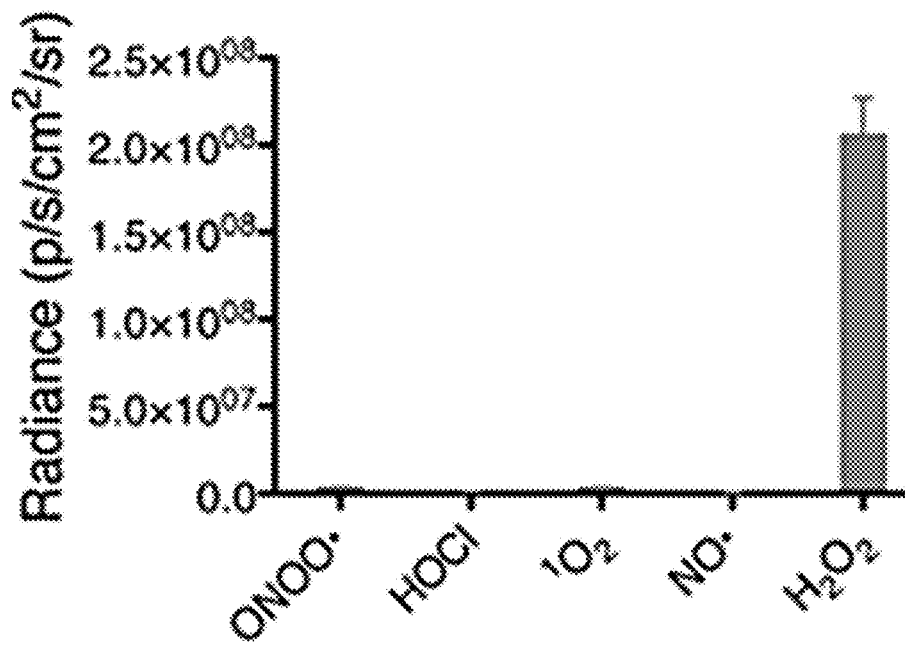
Figure 2F:
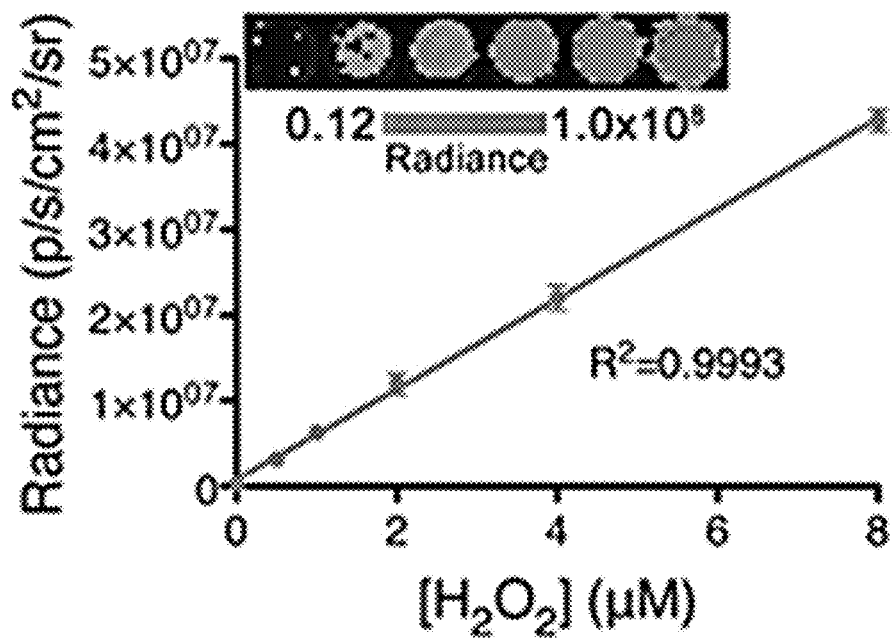

Likewise, the chemiluminescence response of CF-SPN to various ROS and RNS was assessed without any external light excitation (FIG. 2E), demonstrating that luminescence through CRET was only detected in the presence of $H_2O_2$. This specific luminescence response was shown to linearly correspond to environmental $H_2O_2$ (FIG. 2F). The chemiluminescence limit of detection of $H_2O_2$ under the experimental conditions was 5 nM. A prolonged generation of luminescence was observed in vitro, with a signal half-life of approximately 80 minutes (FIG. 7).

CF-SPNs of the disclosure exhibit the sensitivity at levels of both the fluorescence (FIG. 2D) and chemiluminescent channels (FIG. 2F) desirable for the detection of the nanomolar changes in oxidative and nitrosative species that are generated during pathophysiological conditions in vivo. Accordingly, the specific, simultaneous discrimination of the presence of ONOO/HOCl and $H_2O_2$ is possible through the application of CF-SPN to fluorescence ratiometric and chemiluminescence imaging, respectively.

In Vivo Longitudinal Imaging of APAP-Induced Hepatotoxicity with CF-SPN:

Prior to application of CF-SPN for in vivo drug hepatotoxicity imaging, performance parameters of the nanoprobe were further scrutinized, as illustrated in FIGS. 7A-7C, 8A, and 8B. CF-SPN were incubated in undiluted mouse serum at 37° C., and the 680 nm/820 nm fluorescence emission ratio, as well as the luminescence emission, were assessed over time (FIG. 7B).

There was no change to the fluorescence ratio during the 4 h of incubation. However, a gradual consumption of CPPO was noted, reaching a plateau by 2 h of incubation. This data indicates that imaging desirably occurs within 1 h of CF-SPN administration. Since optical imaging is limited by the penetration of light through tissue, the depth of imaging penetration of CF-SPN is advantageous for interrogation of deep, absorbing tissue such as the liver. The depth of imaging penetration following incubation of CF-SPN with $H_2O_2$ was assessed using a tissue-mimicking gel phantom composed of gelatin, hemoglobin, and intralipid, as described in Shuhendler et al., (2011) ACS Nano 5: 1958-1966, incorporated herein by reference in its entirety. By overlaying various thicknesses of gel phantom, the penetration of the luminescent signal from CF-SPN was found to be at least 2.5 cm of gel depth (FIG. 7C).

Liver targeting of galactose-conjugated SPN nanoprobes of the disclosure (Gal-SPN) was assessed relative to an SPN formulation without a targeting ligand attached thereto (PEG-SPN) (FIGS. 8A and 8B), where both probes were composed only of PFODBT and PS-PEG, but also with and without galactose, respectively. Upon necropsy, a selective and significant liver accumulation of Gal-SPN (FIG. 8A, top) was seen relative to PEG-SPN (FIG. 8A, bottom) and confirmed after quantitation of SPN fluorescence (p<0.05) (as in FIG. 8B). With this confirmation of sensor stability, good imaging depth of penetration, and significant hepatic accumulation through galactose targeting, CF-SPN nanoparticles were assessed for their ability to monitor drug-induced hepatotoxicity in real-time.

APAP-induced hepatotoxicity is well characterized in mice in terms of threshold dose response and metabolic modulators that remediate toxic outcome, as described by McGill & Jaeschke ((2013) Recent Adv. Relation to Hepatotoxicity Diagnosis. Pharm Res.), and thus serves as an ideal model of liver toxicity with which to validate CF-SPN. Female nude mice were administered a given dose of APAP intraperitoneally, anesthetized, and fitted with tail vein catheters.

Sequential fluorescent and luminescent images were acquired immediately following administration of 0.8 mg CF-SPN (FIG. 3). Chemiluminescent images show a significant enhancement in signal by 18 min following the commencement of imaging with an APAP overdose (300 mg/kg). However, only baseline luminescence similar to untreated mice (control) was detected following lower drug doses (150 mg/kg and 75 mg/kg) (FIG. 3A, top). This threshold dose-type toxicity is in good agreement with manifestation of APAP-induced hepatotoxicity in mice (Srivastava et al., (2010) Handbook Exp. Pharmacol. pp 165-194; Reese et al. (2011) Chem. Biol. Interact. 192: 60-64; McGill & Jaeschke (2013) Recent Adv. Relation to Hepatotoxicity Diagnosis. Pharm Res.).

Figure 3A:
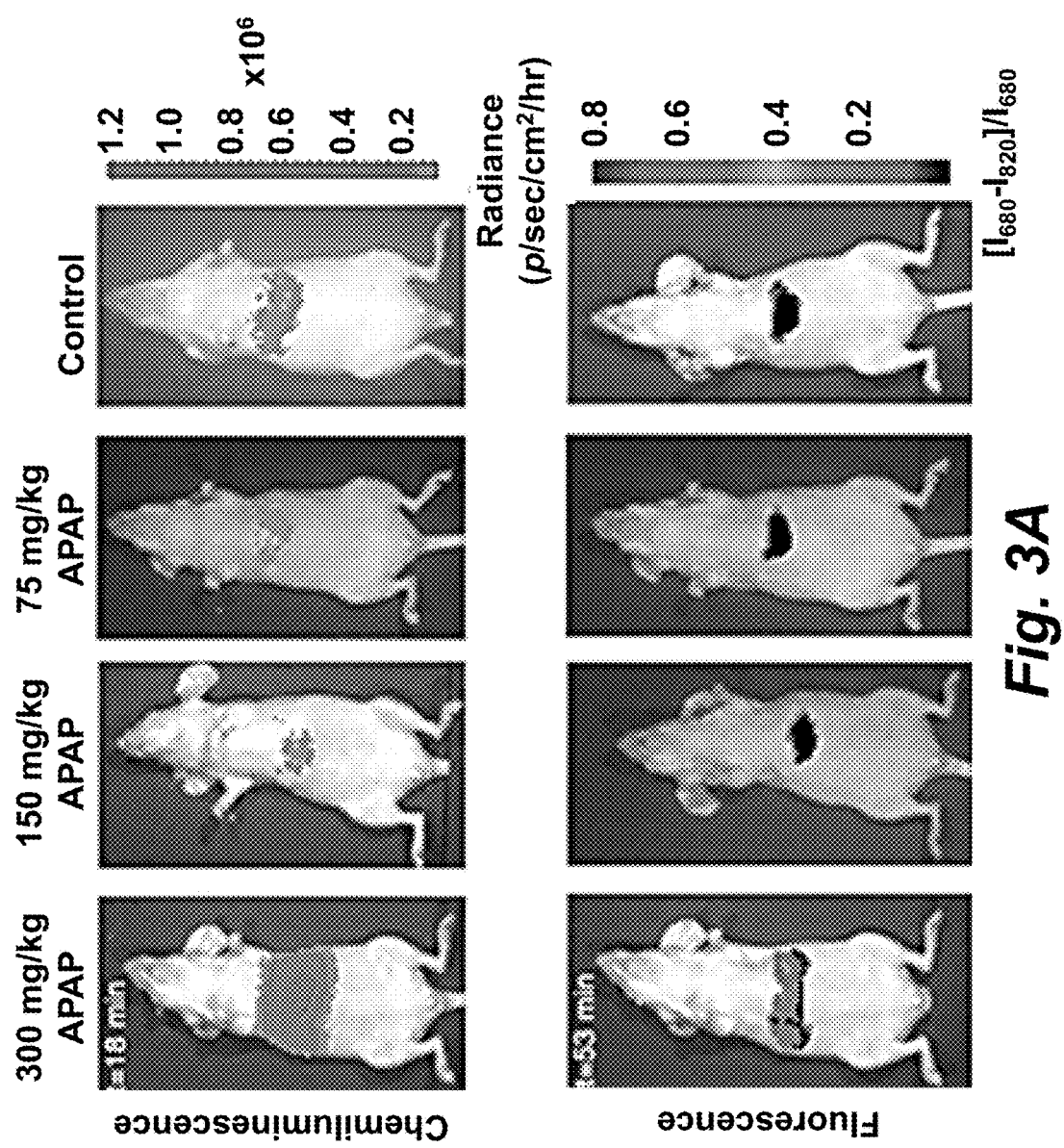
FIGS. 3A-3E illustrate real-time in vivo imaging of hepatotoxicity threshold following APAP administration to mice.
Figure 3B:
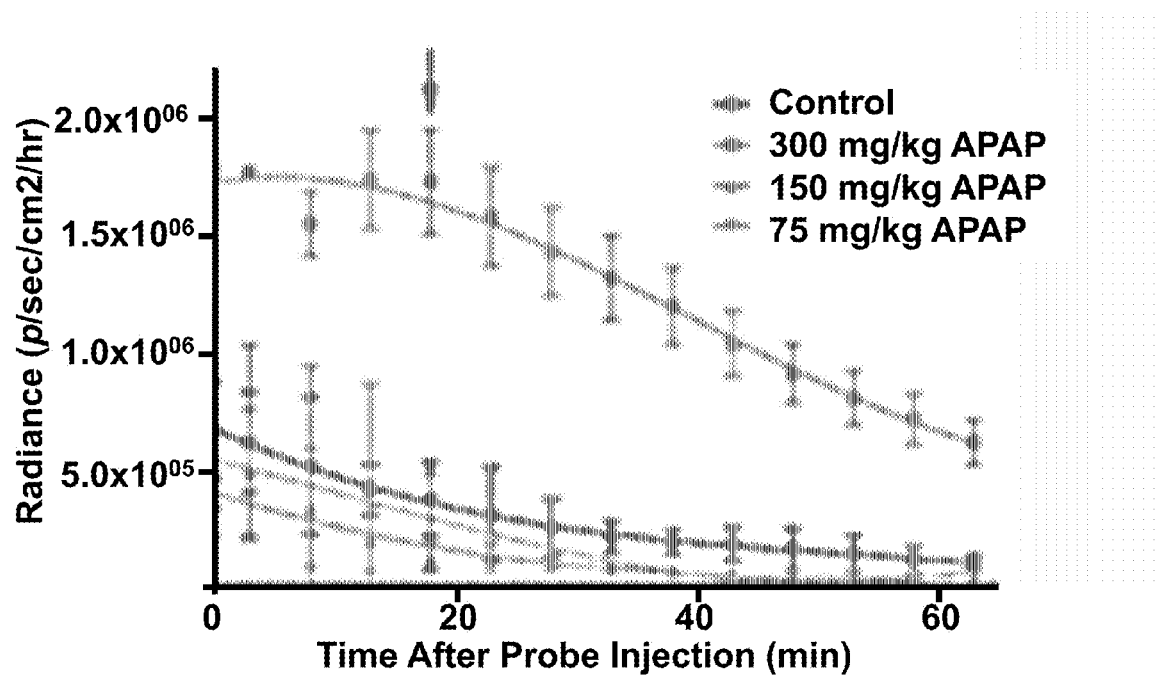
Figure 10A:
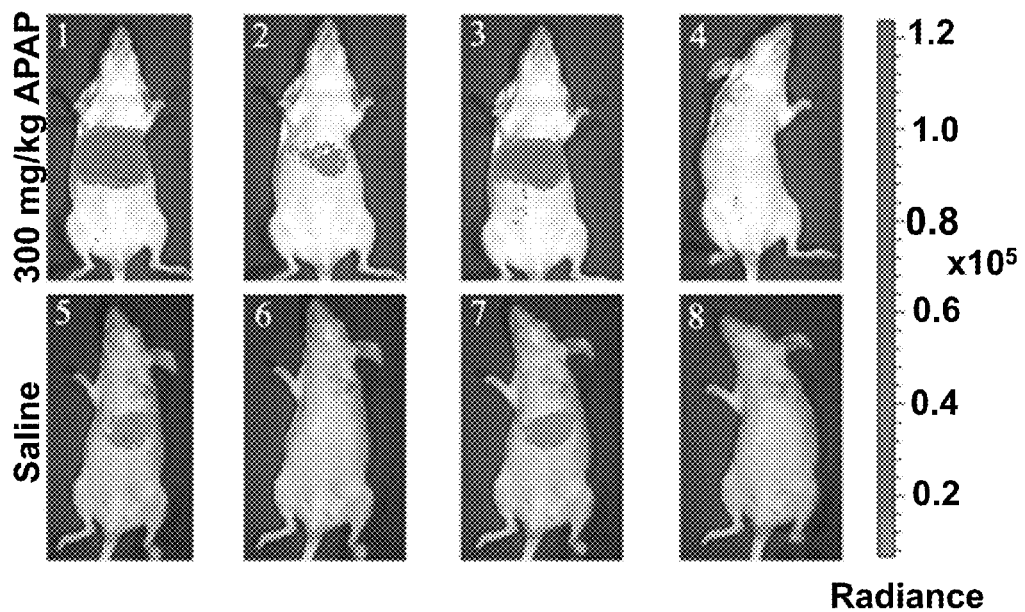
FIG. 10A illustrates extension luminescent images of the time course of H₂O₂ detection after drug challenge by readministration of CF-SPN. Mice were administered 300 mg/kg APAP (top row, 1-4) or saline (bottom row, 5-8) i.p., followed by the administration of 0.8 mg CF-SPN i.v. After 25 min, CF-NP was readministered i.v.
Figure 10B:
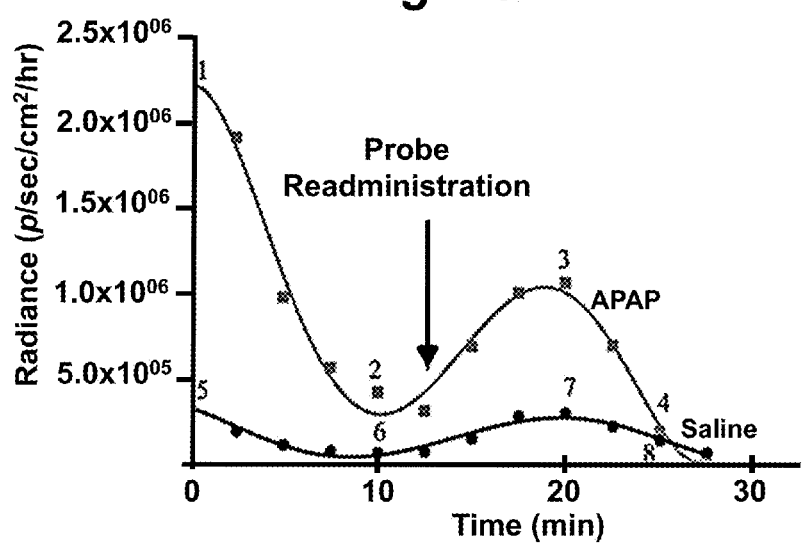
FIG. 10B is a graph illustrating the quantitation of liver luminescence. Black arrow in indicates CF-SPN readministration. Numbers on images correspond to time points indicated on plot.

This elevation in luminescence from APAP overdose was sustained over the time course of imaging (FIG. 3B). However, due to the baseline consumption of CPPO that had been observed in mouse serum (FIG. 7B), the ability to extend the $H_2O_2$ detection window with the re-administration of CF- SPN was assessed (FIG. 10). The re-administration of CF-SPN following treatment with a hepatotoxic dose of APAP (300 mg/kg) produced an elevated luminescence signal having approximately 50% of the intensity of the initial CF-SPN injection. In conjunction with only a nominal increase in luminescence in a control animal, this data suggests that extending the period within which $H_2O_2$ can be detected is possible through re-administration of CF-SPN, and that a significant decrease in $H_2O_2$ production occurs within 60 min of the administration of APAP.

Figure 3C:
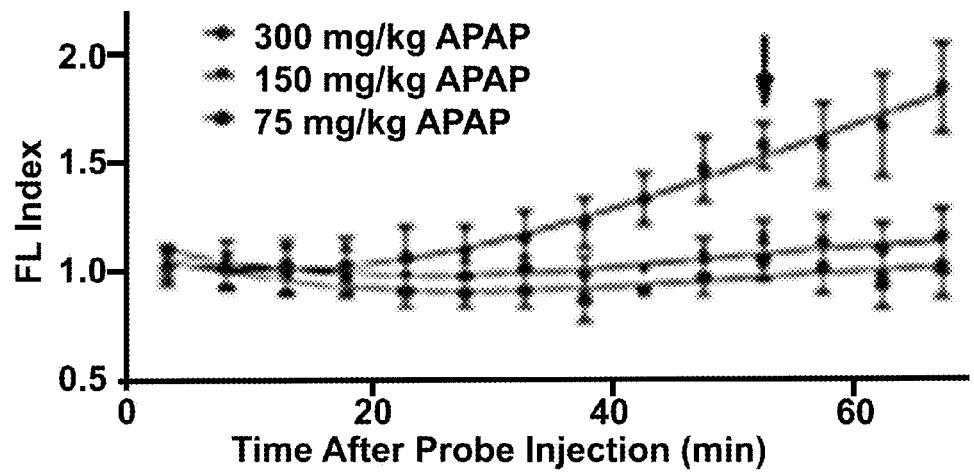

The same threshold toxicity noted from the luminescence channel was observed using the fluorescence channel (FIG. 3A, bottom), in which an elevation in the percent difference between the fluorescence emission intensity at 680 nm and at 820 nm (due to loss of the 820 nm signal) at 53 min after CF-SPN administration was only observed for mice receiving 300 mg/kg APAP. Quantitation of the fluorescence ratiometric signal required normalization of the percent difference values in APAP-treated mice to those of the control mice, yielding the fluorescence index (FL index) (FIG. 3C). This normalization accounted for changes in the fluorescence percent difference metric due to the combination of nanoparticle accumulation in liver tissue over time and the non-linear variation in imaging depth of penetration afforded to light emitted at 680 nm versus 820 nm. A positive departure of the FL Index from a value of unity indicates an increase in ONOO/HOCl generation, whereas a negative departure indicates a reduction in ONOO/HOCl relative to control animals. With this metric, the increase in ONOO/HOCl generation with APAP overdose was shown to occur later than the generation of $H_2O_2$.

Figure 3D:
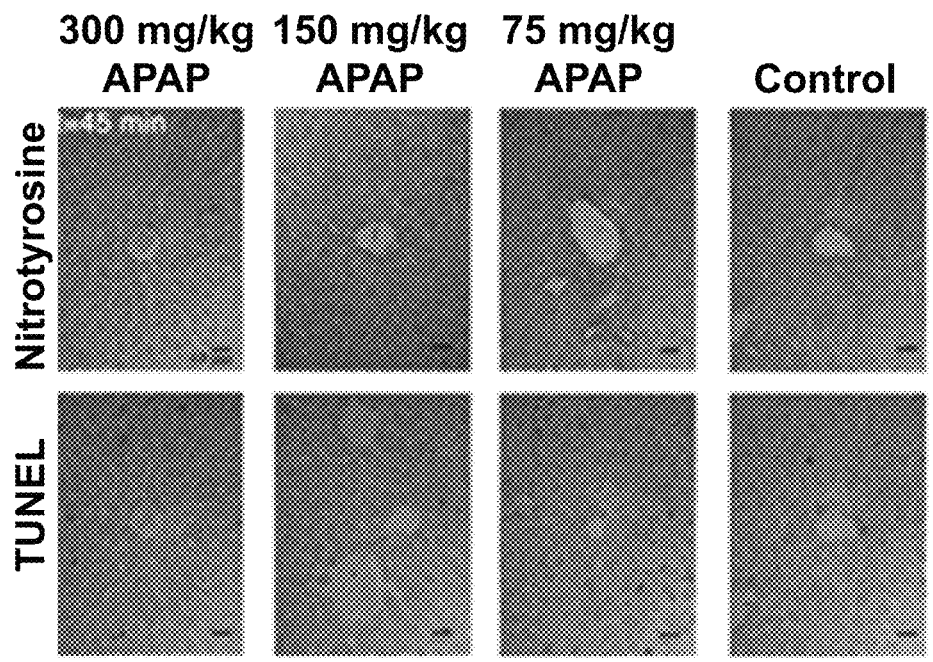
Figure 3E:
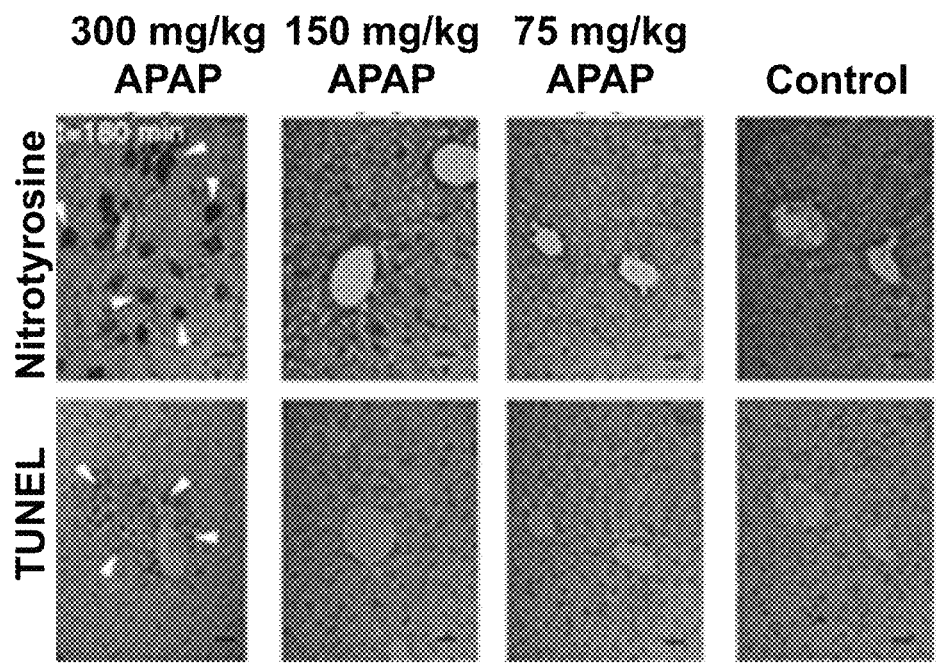
Figure 11:
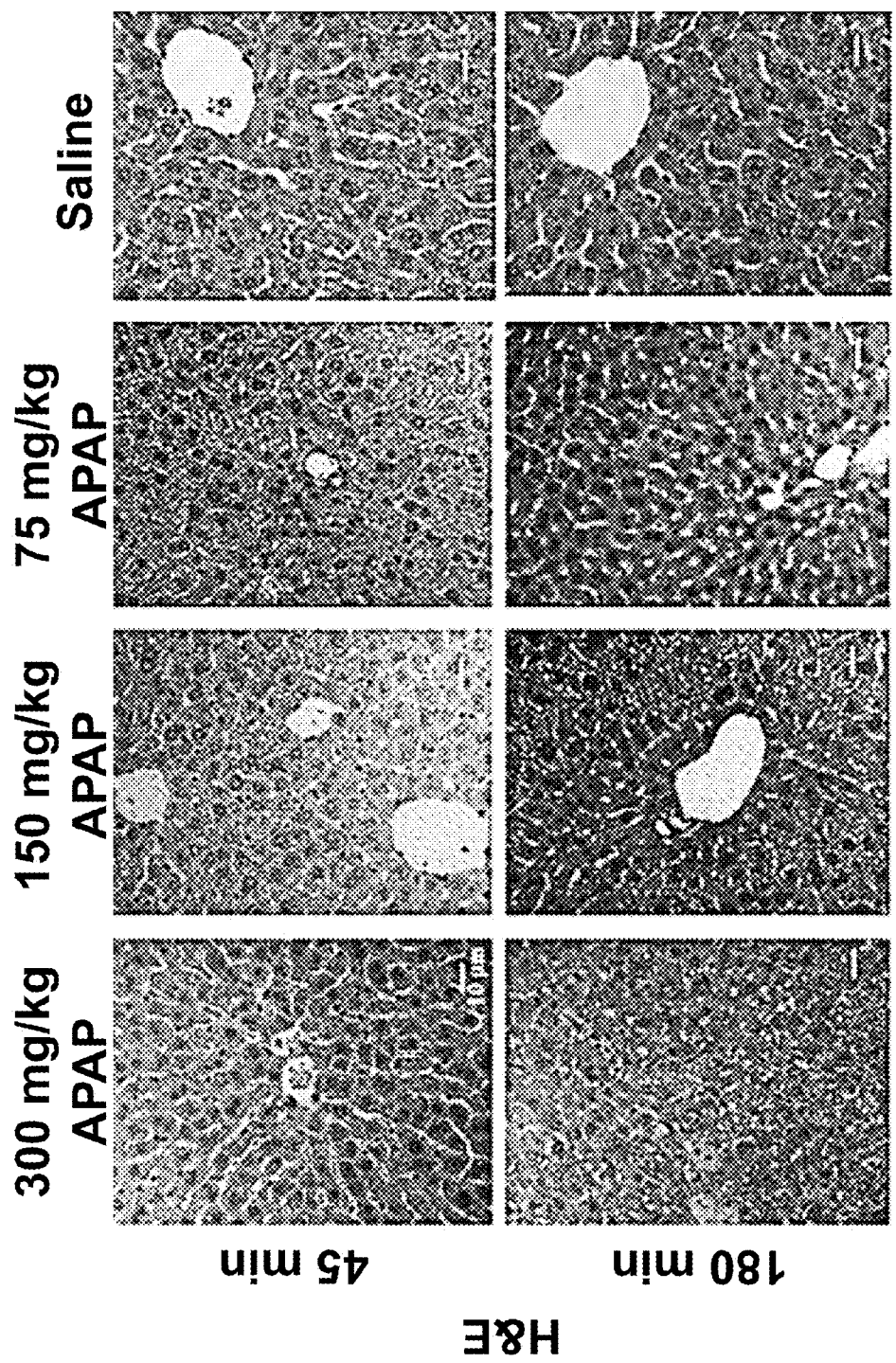
FIG. 11 illustrates an histological analysis of liver tissue. Mice were treated, from left to right, with 300 mg/kg APAP, 150 mg/kg APAP, 75 mg/kg APAP, or saline, and were euthanized 45 min (top row) or 180 min (bottom row) after drug administration. Sections were stained with hematoxylin and eosin. Scale bar represents 10 µm.

The correlation of an imaging biomarker with histological changes in the tissue of interest is desirable to validate the use of a biomarker for indicating an intended pathological outcome. To this end, histological and immunohistochemical analysis of liver tissue was performed on mice 45 min (FIGS. 3D and 11) and 180 min (FIGS. 3E and 11) following treatment with the indicated doses of APAP. No histological changes were noted in liver tissue 45 min after drug challenge at any dose level with hemotoxylin/eosin staining (FIG. 11). Likewise, no foci positive for nitrosative stress, as measured by immunohistochemistry against protein nitrotyrosyl residues, or DNA fragmentation indicative of hepatocyte cell death, as indicated by TUNEL staining, were observed at 45 min (FIG. 3D). However, at 180 min following APAP administration, significant protein nitrotyrosyl and TUNEL-positive foci, as well as hepatocellular degeneration characteristic of APAP-induced oncotic necrosis, were observed at the 300 mg/kg dose level (FIGS. 3E and 11).

Lower doses of APAP did not induce immunohistochemical or histological changes to liver tissue, which is in agreement with the imaging results of a threshold toxic dose between 150 mg/kg and 300 mg/kg APAP. Therefore, both oxidative (luminescent) and nitrosative (fluorescent) channels of CF-SPN correspond to the previously reported toxic threshold dose of APAP in mice, and correlate with histological and molecular changes indicative of drug-induced hepatotoxicity. Importantly, these results confirm the utility of CF-SPN to detect early hepatotoxicity in vivo, prior to even histological changes in prospectively drug-damaged tissue.

Figure 12A:
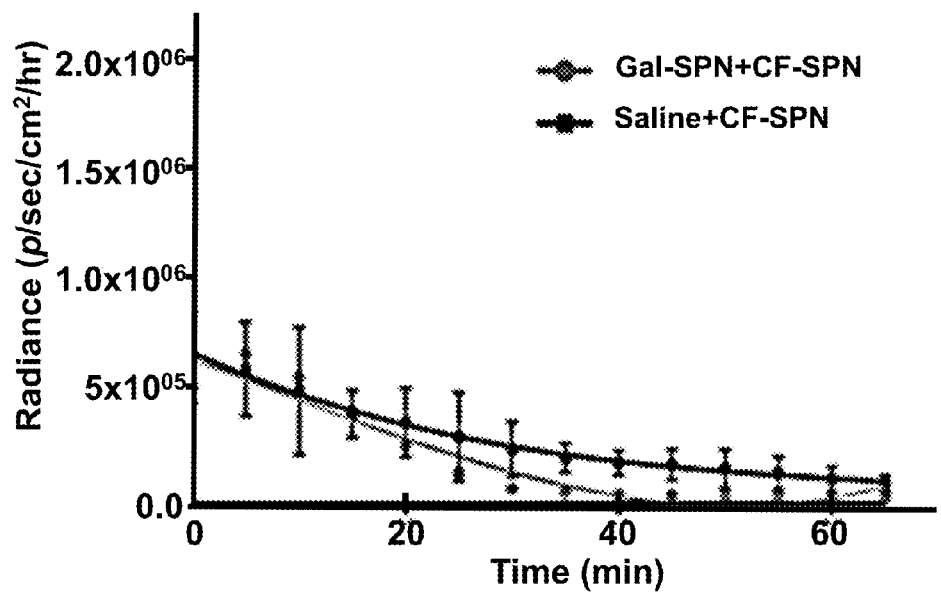
FIGS. 12A and 12B illustrate an in vivo assessment of hepatotoxic potential of administered nanoparticle. The galactose-targeted nanoparticle (Gal-SPN) or saline (black squares) were administered i.v. 15 min prior to CF-SPN, and the chemiluminescence (FIG. 12A) and fluorescence index (FIG. 12B) were recorded. Data represents the mean±s.d. of n=3 mice.
Figure 12B:
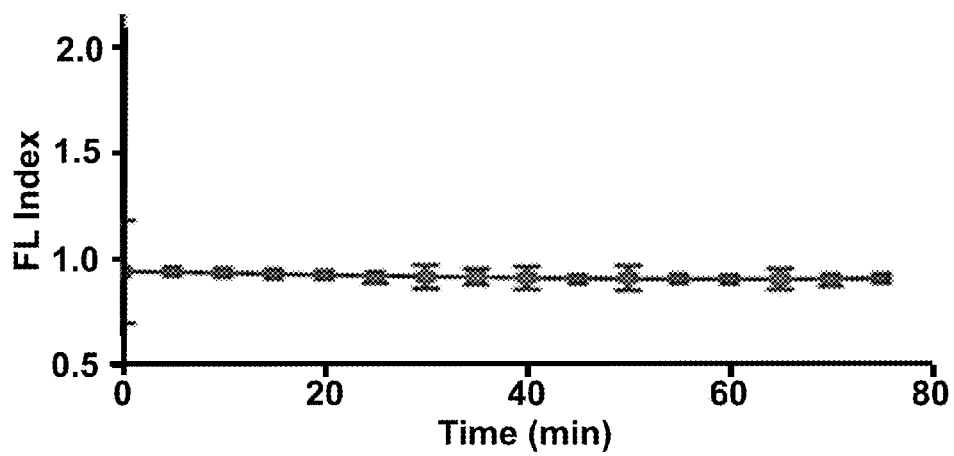

One of the challenges of using nanoprobes to detect ROS and RNS in vivo is the ready generation of these oxidative and nitrosative species by the nanoprobes themselves (Jones & Grainger (2009) *Adv. Drug Deliv. Rev.* 61: 438-456; Maynard et al., (2011) *Toxicol. Sci.* 120 (Suppl 1): S109-29), which can confound the determination of the source of the evolved signal. To systematically interrogate the production of ROS or RNS by the CF-SPNs of the disclosure, mice were administered saline (black squares) or Gal-SPN (red circles) prior to administration of CF-SPN (FIGS. 12A and 12B). Since a dose-response relationship has been reported for the generation of ROS or RNS by nanoparticles, regardless of the size or formative material, an elevated degree of baseline activation of CF-SPN would be expected following a prior dose of Gal-SPN relative to saline control if CF-SPN induced the production of significant amounts of ROS or RNS in the liver. However, upon pre-dosing with Gal-SPN, neither the luminescent (FIG. 12A) nor the fluorescence index (FIG. 12B) channels indicated any significant production of either $H_2O_2$ or ONOO/HOCl, respectively, relative to saline-treated animals.

Figure 9A:
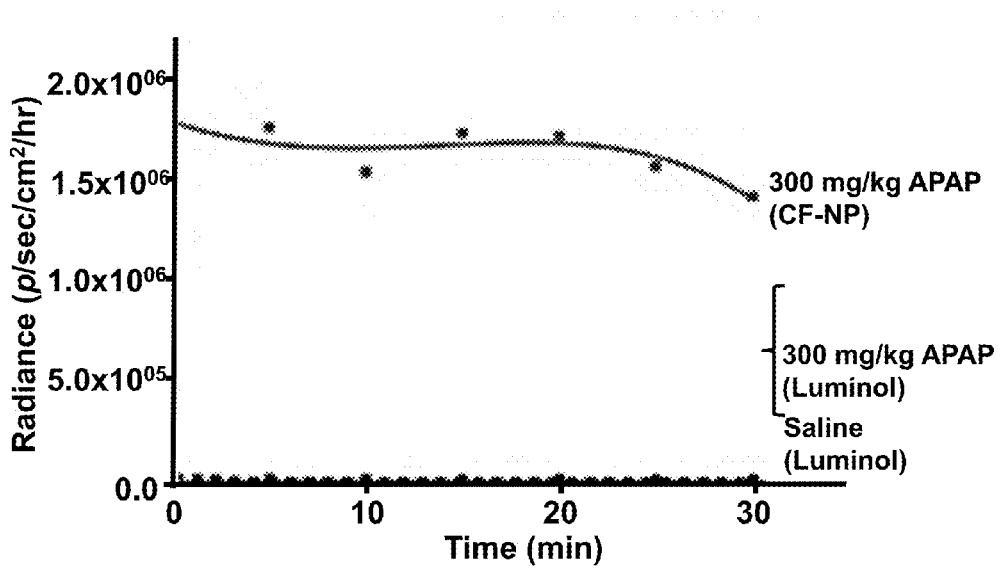
FIGS. 9A and 9B illustrate a comparison between luminol and CF-SPN for their ability to detect drug-induced liver production of H₂O₂. Mice were administered 300 mg/kg APAP i.p., followed either by 0.8 mg CF-SPN i.v., which contained 0.2 mg CPPO, or 0.2 mg luminol i.v.
Figure 9B:
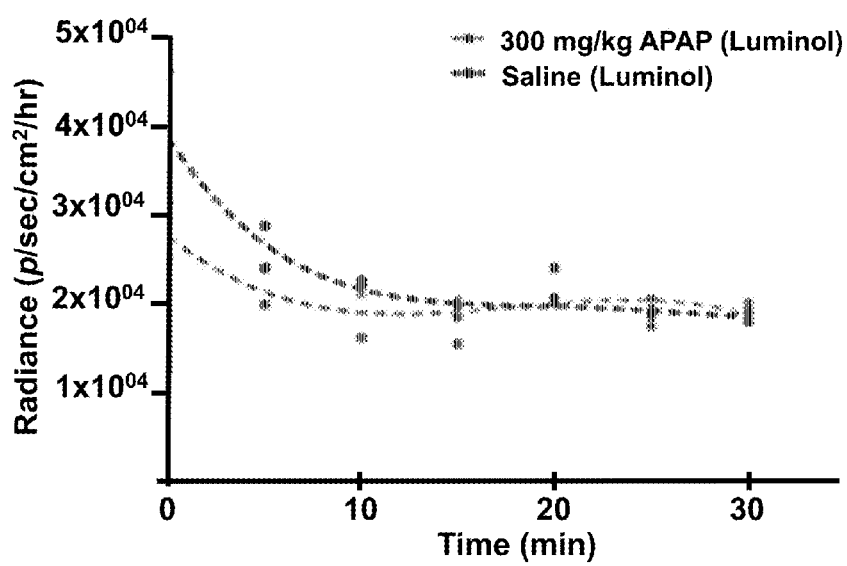

Additionally, the ability of luminol, a small molecule blue-emitting chemiluminescent reporter commonly applied to $H_2O_2$-sensing to indicate hepatic oxidative stress following APAP overdose, was assessed. Luminol did not produce any detectable luminescent signal at a dose equal to an administered dose of CPPO encapsulated in CF-SPN (FIGS. 9A and 9B). This is likely due to the high local concentration of CPPO in CF-SPN in combination with the efficient CRET to the near infrared-emitting PFODBT, resulting in a more sensitive imaging probe spectrally tuned for in vivo deep tissue imaging. This data both validates the use of CF-SPN as a biologically inert nanoprobe for the in vivo detection of ROS and RNS, and further reflects the biocompatibility of semiconducting polymers as biomedical materials.

Figure 4A:
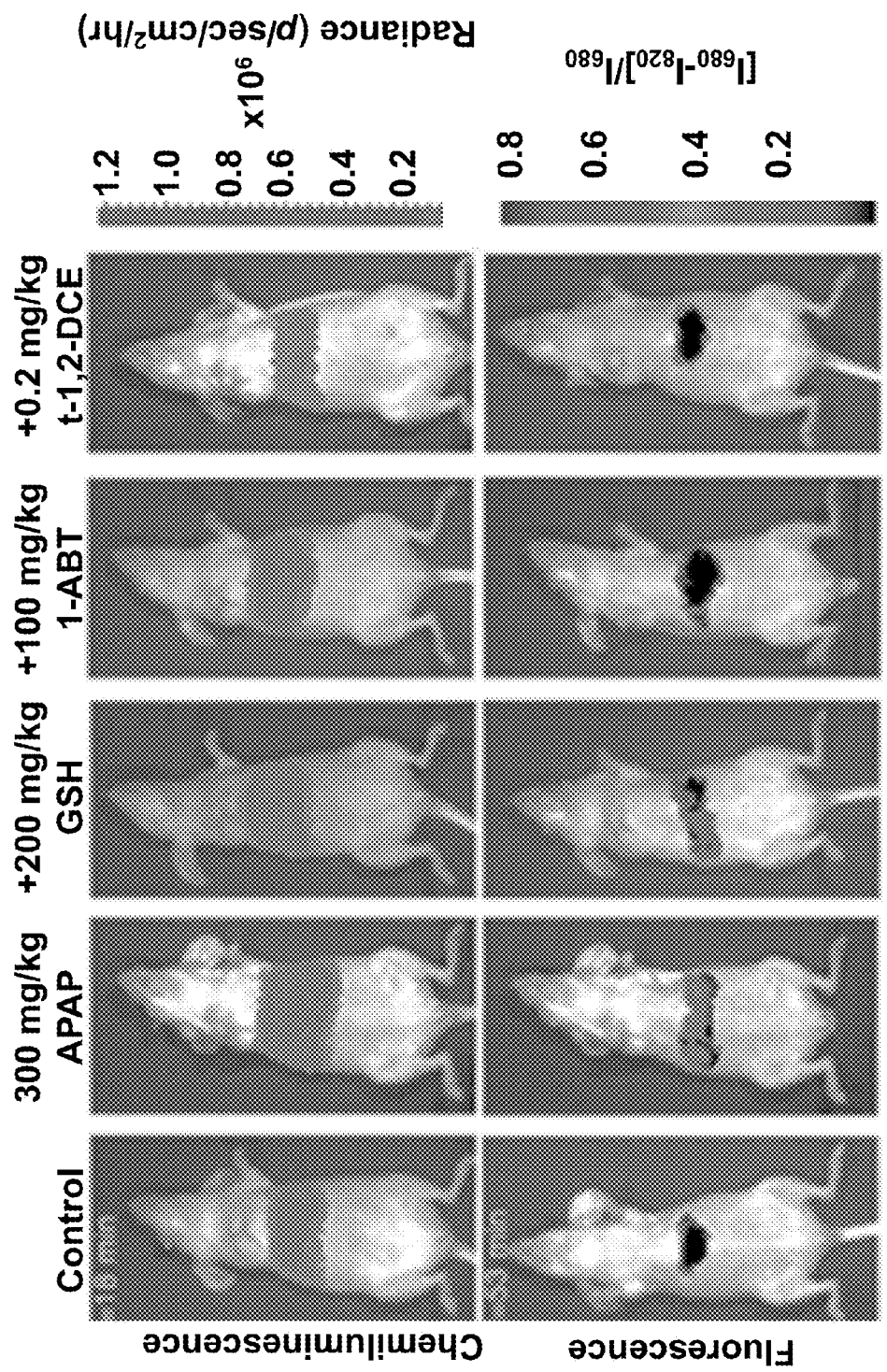
FIGS. 4A-4D illustrate longitudinal in vivo monitoring of the remediation of APAP-induced hepatotoxicity with enzyme inhibitors and antioxidant scavengers.

Monitoring the Modulation of APAP-Induced Hepatotoxicity:

The ability to determine the hepatotoxic potential of a drug candidate is equally as important to the ability to investigate the mechanism of any observed toxicity. To this end, the effects of inhibitors of APAP bioactivation on in vivo hepatic ROS and RNS production were evaluated using the CF-SPNs of the disclosure (FIGS. 4A, 4C, and 4D).

Figure 4B:
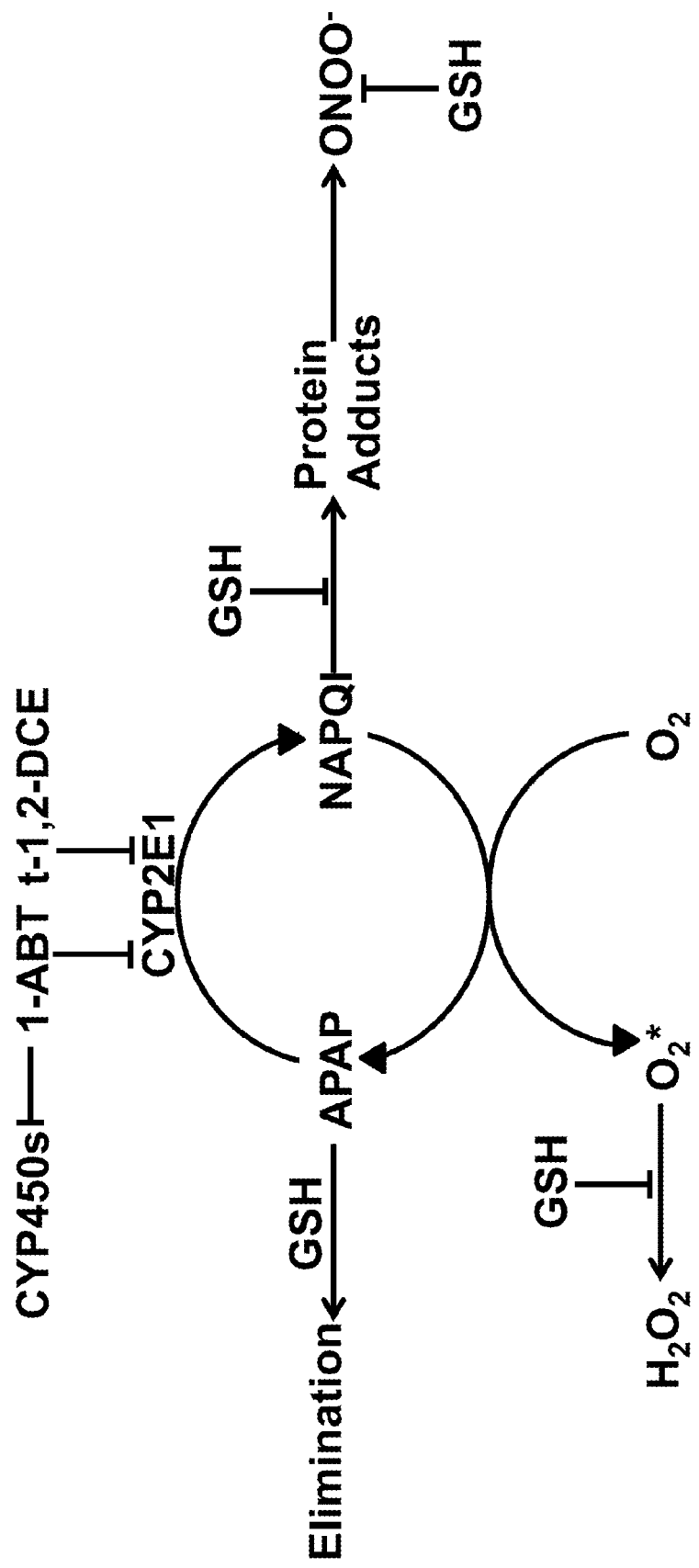

Without wishing to be bound by any one theory, a mechanism for APAP bioactivation involves CYP450-mediated oxidation to an iminoquinone, N-acetylparaquinonimine (NAPQI), which can bind directly to cellular proteins to induce mitochondrial dysfunction and the production of ONOO, or undergo reduction by molecular oxygen to form superoxide ($O_2.^-$) and $H_2O_2$ (FIG. 4B). This pathway of bioactivation was inhibited by the administration of glutathione (GSH), an antioxidant and nucleophilic scavenger of reactive metabolites such as NAPQI and ROS/RNS, 1-aminobenzotriazole (1-ABT), a broad spectrum suicide inhibitor of CYP450 enzymes, and trans-1,2-dichloroethylene (t-1,2-DCE), a specific inhibitor of CYP2E1, which is the CYP450 isoform responsible for the majority of Phase I metabolism of APAP.

A reduction of luminescence emission (FIGS. 4A and 4C) and a reduction of the FL index towards unity (FIGS. 4A and 4D) was observed with all three inhibitors of APAP bioactivation, indicating the successful remediation of oxidative and nitrosative stress, respectively. However, there were differences in the magnitude and time course of remediation between the inhibitors employed. The administration of GSH, which has been shown to be superior to N-acetylcysteine as an antidote to APAP toxicity in mice, resulted in a reduced level of $H_2O_2$ and ONOO/HOCl production relative to mice receiving APAP alone, but still elevated relative to mice receiving either 1-ABT or t-1,2-DCE (FIGS. 4C & 4D). Additionally, both 1-ABT and t-1,2-DCE suppressed ONOO/HOCl production to the same extent (FIG. 4D).

Figure 4C:
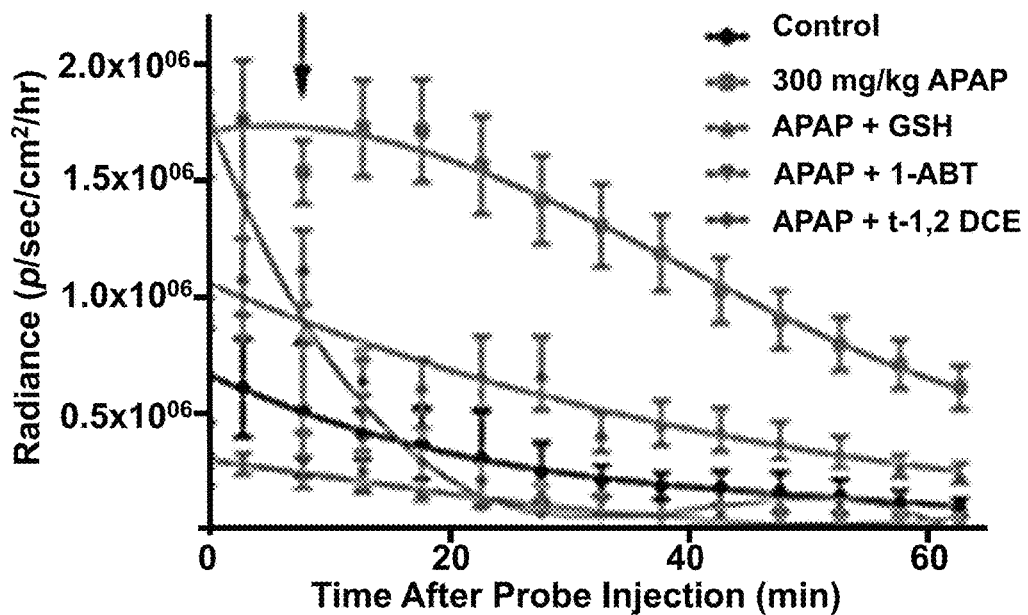
Figure 4D:
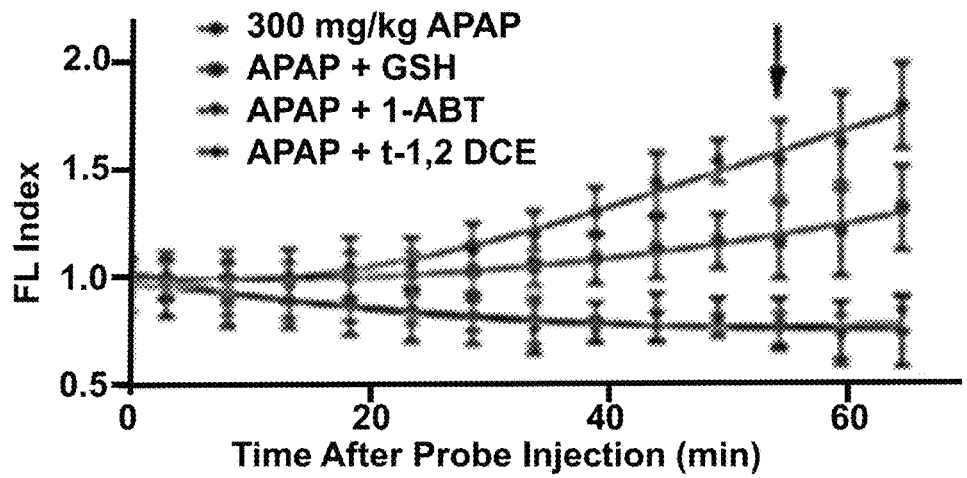

However, t-1,2-DCE was able to completely prevent $H_2O_2$ production, while an intense but short-lived (less than 20 min after CF-SPN administration) production of $H_2O_2$ was observed following 1-ABT treatment (FIG. 4C). Accordingly, using CF-SPN, both the magnitude and time-course of the chemical modulation of drug-induced oxidative and nitrosative stress can be obtained longitudinally and in the natural microenvironment of the liver in intact animals.

Longitudinal Monitoring of INH Hepatotoxicity:

Tuberculosis is a global health problem most often and most effectively managed with chemotherapy. CF-SPN nanoprobes according to the disclosure applied to monitor the hepatic oxidative and nitrosative stress produced in mice following treatment with the most widely used anti-tuberculosis chemotherapy agent, INH, which is associated with hepatotoxicity in as many as 25% of patients (FIG. 5).

Figure 5A:
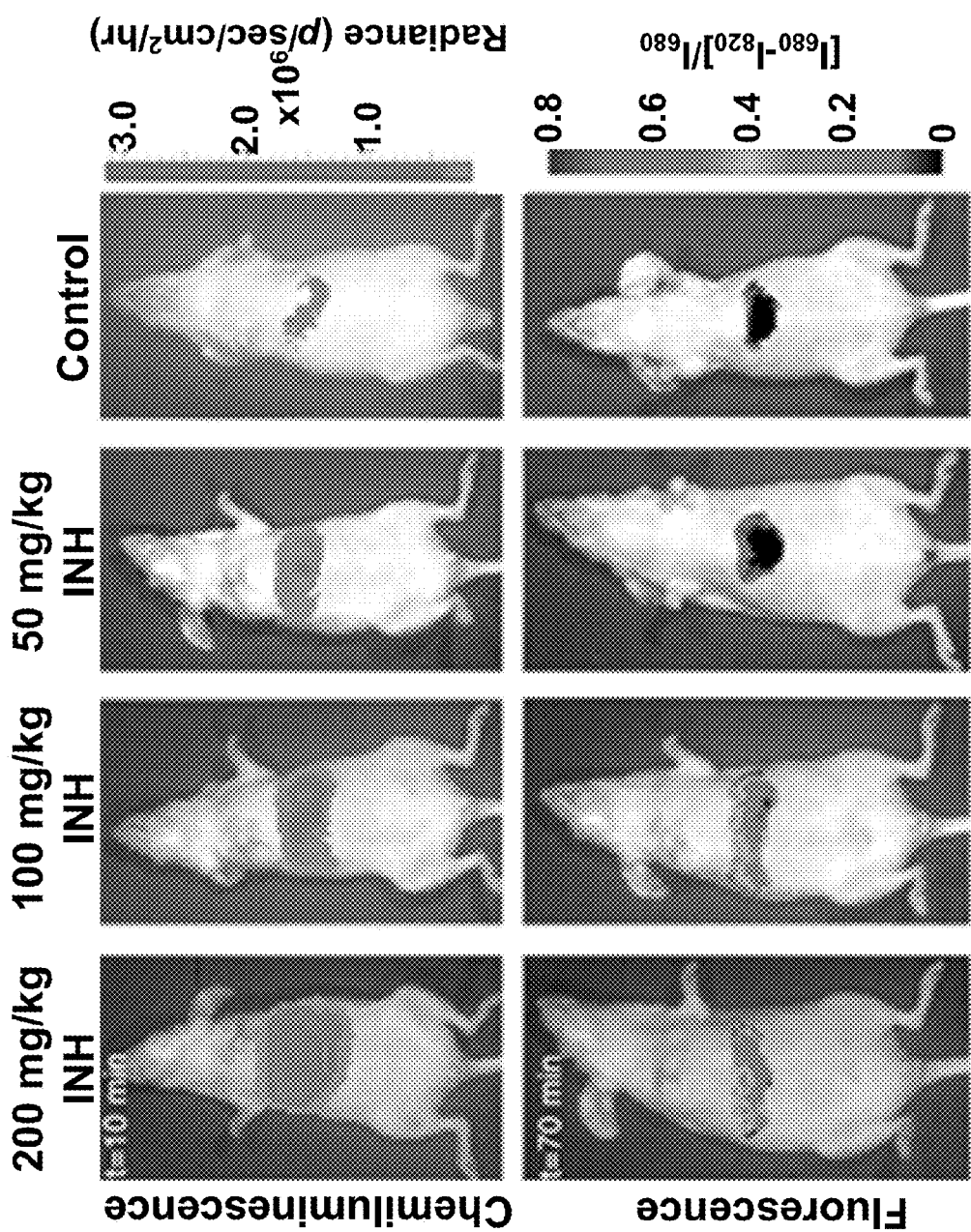
FIGS. 5A-5D illustrate real-time in vivo imaging of dose-dependent hepatotoxicity following INH administration to mice.
Figure 5B:
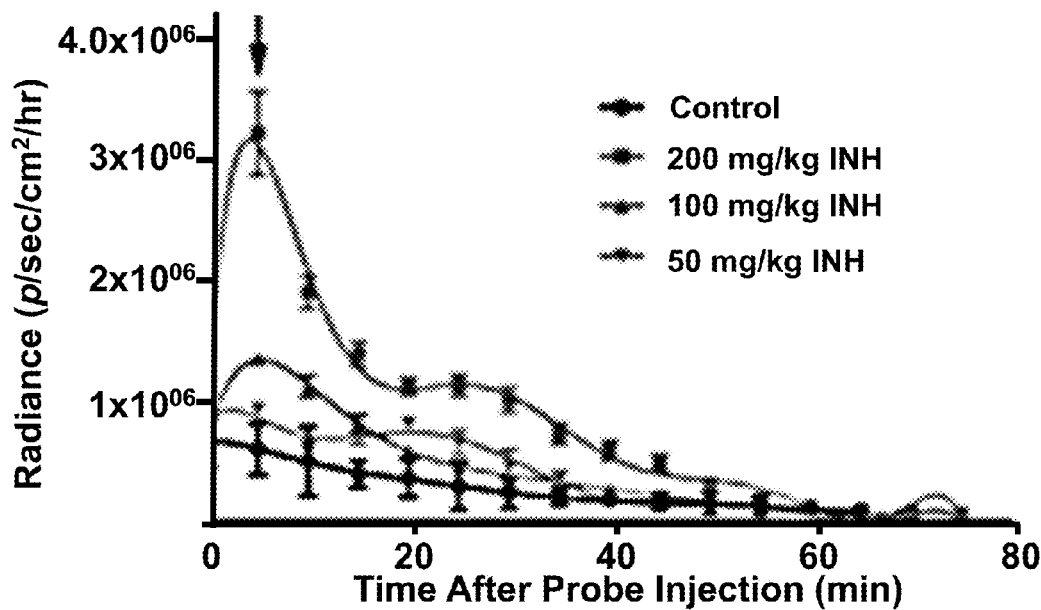
Figure 5C:
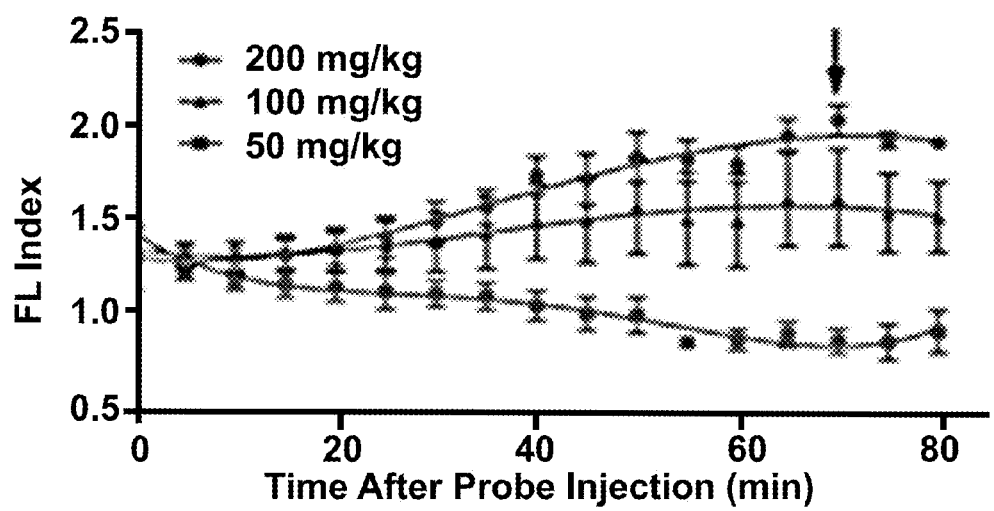

Female nude mice were intraperitoneally administered a given dose of INH, anesthetized, and fitted with tail vein catheters. Sequential fluorescent and luminescent images were acquired immediately following administration of CF-SPN (0.8 mg). Unlike the threshold toxicity observed with APAP on both chemiluminescent and fluorescent channels (FIGS. 3A-3D), INH exhibited a dose-dependent enhancement of ONOO/HOCl production (FIGS. 5A and 5C), but a threshold dose-type production of $H_2O_2$ (FIGS. 5A and 5B). Additionally, the kinetics of both oxidative and nitrosative stress differed significantly between APAP and INH, with INH inducing a more short-lived oxidative burst (FIG. 5B) and a more rapidly developed and sustained induction of nitrosative stress (FIG. 5C). Therefore the longitudinal, in situ monitoring of drug-induced hepatotoxicity with CF-SPN can reveal variations in timing, magnitude, and dose-dependence of toxic outcomes, such as oxidative or nitrosative stress.

Figure 5D:
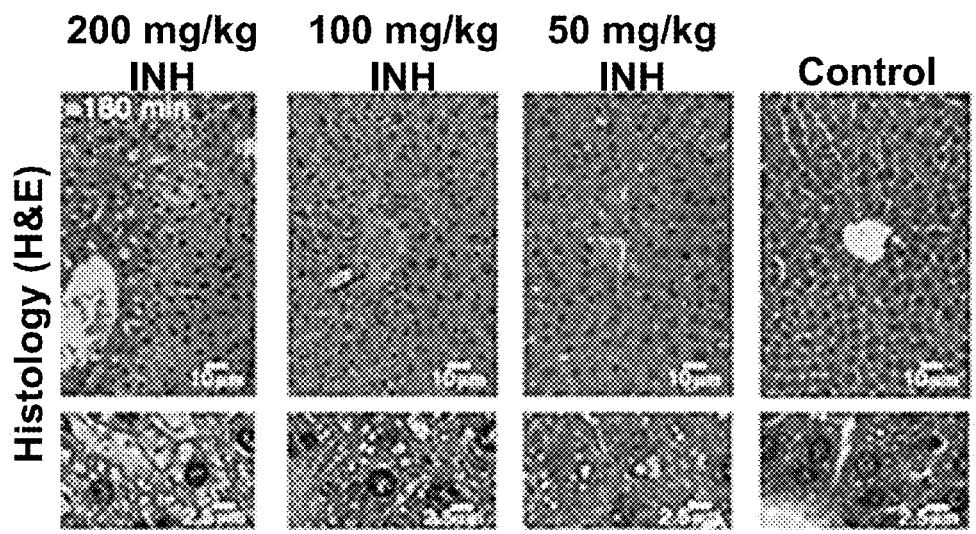

These variations, can be telling of both the mechanism of drug activation and of the sub-cellular targets important for toxic outcome. As with APAP, the dose-dependent enhancement of hepatotoxicity as indicated by CF-SPN was correlated with prospective hepatocyte death, as indicated by cell vacuolization and deterioration through histological examination of liver tissues (FIG. 5D). Interestingly, there was a dose-dependent increase in the severity of liver tissue degradation that more closely echoed the dose-dependent generation of ONOO/HOCl (FIG. 5C), not the threshold dose-type generation of $H_2O_2$ (FIG. 5B). These results demonstrate the advantageous application of CF-SPN to the prodromal, longitudinal, and in vivo monitoring of drug-induced hepatic oxidative and nitrosative stress independent of the specific mechanism of drug bioactivation (Phase I versus Phase II), and is not limited to a specific drug class.

The nanoprobes of the disclosure are useful for molecular imaging for drug safety monitoring due to their combination of novel optical materials, as shown in FIG. 1A. Semiconducting polymers known in the art have been used for the development of optoelectronic devices (Mei et al., (2013) *J. Am. Chem. Soc.* 135: 6724-6746; Peet et al., (2007) *Nat. Mater.* 6: 497-500; Sokolov et al., (2012) *Acc. Chem. Res.* 45: 361-371), but their application as biomedical materials is still in its infancy. However, these organic macromolecular fluorophores have been shown to be useful for nanoparticle formulation (Sun et al., (2012) *Nanoscale* 4: 7246-7249; Wu & Chiu (2013) *Angew. Chem. Int. Ed. Engl.* 52: 3086-3109). Advantages include large mass extinction coefficients resulting in efficient fluorescence, excellent acute and subacute polymer biocompatibility equivalent to FDA-approved poly(lactate-co-glycolate), and excellent photostability.

Both quantum dots and small molecule fluorophores undergo chemical degradation by ROS and RNS, such as, but not limited to, $H_2O_2$, HOCl, and ONOO (Wu & Chiu (2013) *Angew. Chem. Int. Ed. Engl.* 52: 3086-3109), while SPNs are resistant to such oxidative chemical bleaching. This characteristic makes SPN an advantageous optical reporter for robust imaging of oxidative and nitrosative stress, limiting the loss of FRET or CRET to the intended analyte sensing and not to self-quenching caused by oxidation.

The especially advantageous ability to simultaneously employ two optical channels (fluorescence and chemiluminescence) for dual analyte sensing was realized by efficient and target-specific FRET and CRET of CF-SPN, as shown in FIGS. 2A and 2B. The broad absorption peak from cyan to orange wavelengths provided for efficient CRET from the $H_2O_2$ sensor CPPO (see FIGS. 2B, 2E, and 2F), and the broad red to NIR emission range facilitated efficient FRET to IR775S in the absence of ONOO/HOCl (FIGS. 2B-D).

Of the CRET-FRET nanoprobes reported previously for in vivo ROS sensing, none is an advantageous alternative to the CF-SPN nanoprobes of the disclosure for hepatotoxicity imaging due to their dependence on quantum dots (Zhang et al., (2013) *Nat. Med.* 19: 500-505) that degrade in oxidative environments, or their limited application through local injection due to their large size (i.e. greater than 500 nm) (Zhang et al., (2013) *Nat. Med.* 19: 500-505). Therefore, the embodiments of the CF-SPN nanoprobes of the disclosure represent an especially advantageous nanoprobe design with the potential to remediate current limitations in drug safety screening, and introduce the concept of molecular imaging as a new tool to study toxicology in vivo.

Current methods of hepatotoxicity screening have limited predictive power since they employ covalent binding to biological molecules as safety biomarkers, which correlates poorly to the hepatotoxic potential of the parent drug, as discussed, for example, in Srivastava et al., (2010) *Handbook Exp. Pharmacol.* pp 165-194; Park et al., (2005) *Ann. Rev. Pharmacol. Toxicol.* 45: 177-202; and Thompson et al., (2011) *Chem. Biol. Interact.* 192: 65-71).

However, the CF-SPN nanoprobes of the disclosure have overcome this limitation by employing radical reactive species as safety biomarkers, which have been hypothesized to more closely correlate with toxic outcome (Russmann et al., (2009) *Curr. Med. Chem.* 16: 3041-3053; Walsh & Miwa (2011) *Ann. Rev. Pharmacol. Toxicol.* 51: 145-167; and Pessayre et al., *Handbook Exp. Pharmacol.* pp 311-365). The data presented here support the use of $H_2O_2$ and ONOO as imaging biomarkers for drug safety evaluation, as: (1) only at overdose levels were there histological (FIG. 7) and immunohistochemical (FIGS. 3D-3E) signs of oncotic necrosis, protein nitration, and DNA fragmentation characteristic of APAP hepatotoxicity, which is a necessary validation of $H_2O_2$ and ONOO as mechanistic markers of the endpoint of interest; (2) both $H_2O_2$ and ONOO appear very early in the induction of liver damage and precede even detectable histological signs of toxicity (FIGS. 3D, 3E, and 5D), a necessary requirement of an effective safety biomarker (Antoine et al., (2008) *Expert Opin. Drug Metab. Toxicol.* 4: 1415-1427); (3) the results obtained using CF-SPN regarding a threshold dose-type centrilobular hepatotoxicity by the production of both $H_2O_2$ (FIGS. 3A and 3B) and ONOO (FIGS. 3A and 3C) are in close agreement with the well-characterized mechanism of APAP toxicity involving both oxidative and nitrosative stress. Further support towards the sensitive reporting of ROS and RNS by the CF-SPN probes of the disclosure was established by the use of enzyme inhibitors and anti-oxidants known to reduce APAP-induced hepatotoxicity (as shown in FIGS. 4A-4D). With the CF-SPN nanoprobes of the disclosure, mechanistic studies of drug-induced hepatotoxicity that were previously only possible in vitro can now be performed in vivo.

Figure 6:
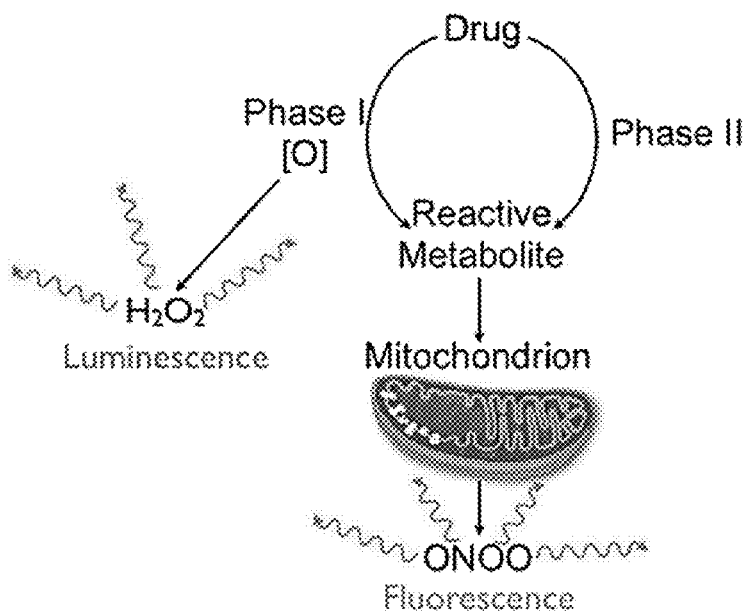
FIG. 6 illustrates proposed differentiation of oxidative and nitrosative stress by CF-SPN to provide mechanistic information on drug bioactivation and resultant hepatotoxicity, wherein the generation of luminescence signal by CF-SPN is mechanistically linked to Phase I oxidative metabolism, which is the major source of $H_2O_2$ following drug challenge. Likewise, a departure of the fluorescence index of CF-SPN from unity can be linked to drug-induced mitochondrial dysfunction, which is the major source of ONOO in hepatotoxicity.
Figure 8B:
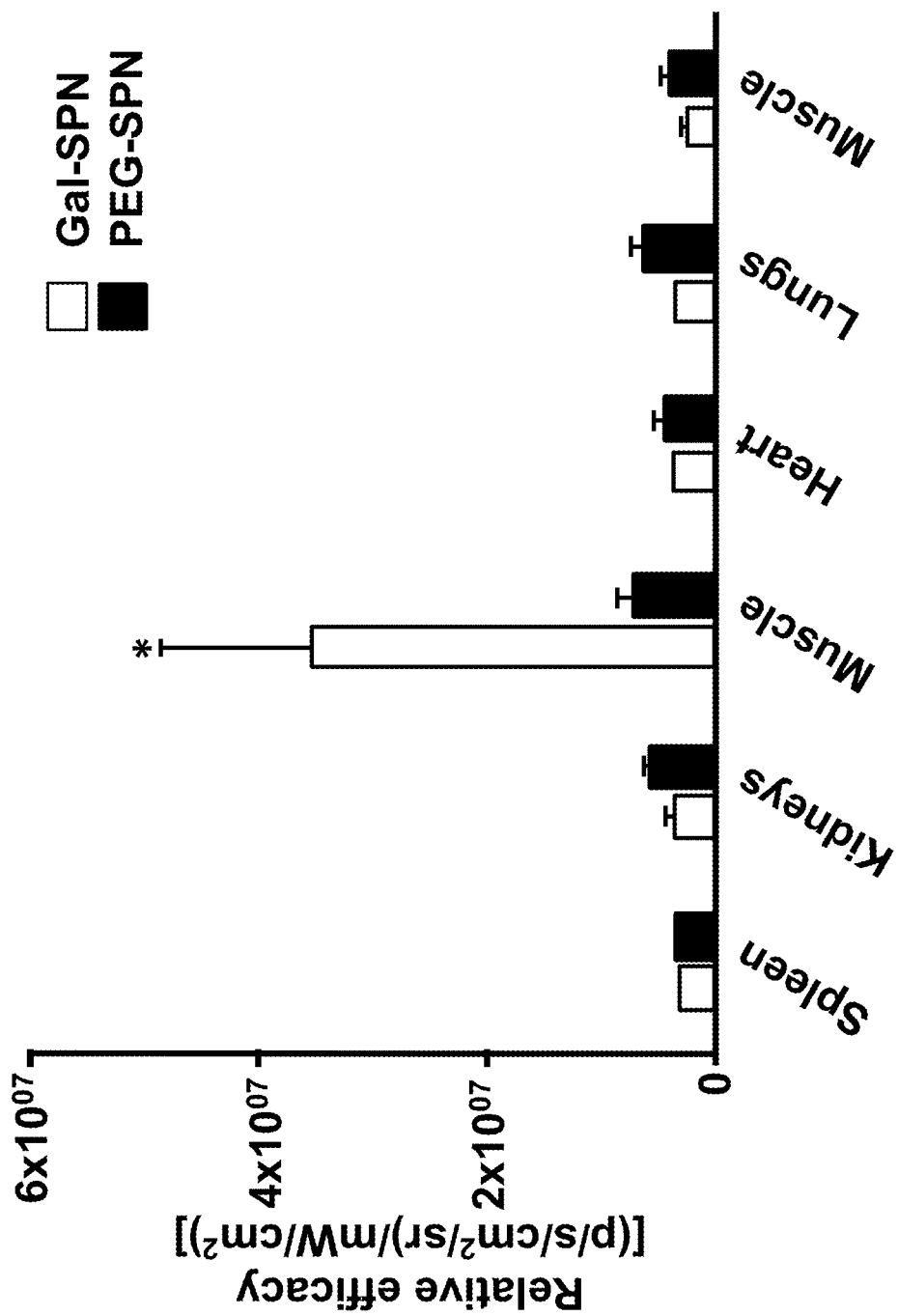

As products of drug metabolism, $H_2O_2$ suggests an elevated production of oxygen radicals derived directly from Phase I oxidation or the reaction of drug metabolites with molecular oxygen (Walsh & Miwa (2011) *Ann. Rev. Pharmacol. Toxicol.* 51: 145-167), where ONOO is more suggestive of either mitochondrial dysfunction or the formation of drug-derived nitrogen radicals (Pacher et al., (2007) *Physiol. Rev.* 87: 315-424; Ghafourifar & Cadenas (2005) *Trends Pharmacol. Sci.* 26: 190-195) (as schematically shown in FIG. 6). Through their differential but simultaneous monitoring, information suggestive of the magnitude and timing of specific pathways of metabolism can be determined, and the relative contribution of oxidative versus nitrosative stress can be gleaned by comparison to histological results.

The value of the two-channel monitoring provided by the CF-SPN nanoprobes of the disclosure is demonstrated when comparing APAP, as shown in FIGS. 3A and 3E, with INH hepatotoxicity (FIGS. 5A-5D). The luminescent (FIG. 3B) and fluorescent channels (FIG. 3C) exhibited a threshold dose-type response following APAP challenge that correlated with histological analysis (FIGS. 3D, 3E, and 5D), suggesting that both oxidative stress and mitochondrial dysfunction contributed to the observed hepatotoxicity.

Following INH challenge, only the fluorescent channel exhibited a classical dose dependent-type response (FIG. 5C) that agreed with the dose-dependent increase in liver degeneration observed through histological analysis (FIG. 5D), while the luminescent channel exhibited a threshold dose-type dependence (FIG. 5B). Even though INH challenge resulted in both oxidative and nitrosative stress, the correlation of histology with the dose-response relationship of the fluorescent channel indicates a mechanistic role for ONOO generation and mitochondrial dysfunction in INH hepatotoxicity in vivo.

While the mechanism of INH toxicity remains incompletely characterized, this result is supported by new evidence that increasingly suggests the involvement of mitochondrial impairment following INH bioactivation (Li et al., (2013) *Nat. Med.* 19: 418-420; Chowdhury et al., (2006) *J. Hepatol.* 45: 117-126), and by the potentiation of hepatotoxicity in humans deficient in acetylation capacity (Metushi et al., (2011) *Clin. Pharmacol. Ther.* 89: 911-914; Lauterburg et al., (1985) *J. Pharmacol. Exp. Ther.* 235, 566-570), which is a Phase II but not Phase I metabolic pathway linked to INH toxicity. Therefore, the simultaneous and differential imaging of $H_2O_2$ and ONOO uniquely provided by CF-SPN is advantageous for in vivo mechanistic studies of drug-induced liver injury. The degree of mechanistic information provided by the CF-SPN nanoprobes of the disclosure is useful for the redesign of drug candidates to avoid specific pathways of bioactivation, and for the selection of mechanistic remediation strategies. With this information, both the fruitless pursuit of truly toxic new chemical entities and the premature elimination of potentially effective compounds can be significantly reduced.

Thus, the compositions and methods of the disclosure are suitable for real-time, longitudinal, and in vivo assessment of drug-induced hepatotoxicity. These goals have been realized using CF-SPN, a novel nanoprobe capable of two-channel optical imaging. Materials conferring on the nanoprobe stability and robustness for in vivo imaging of oxidative and nitrosative stress was demonstrated, and the mechanistic value of simultaneously and differentially monitoring $H_2O_2$ and ONOO/HOCl was afforded in the context of providing new evidence regarding the mechanism of INH hepatotoxicity. The CF-SPN nanoprobes of the disclosure can thus serve the specific purpose of drug safety screening throughout the body's tissues for the express purpose of remediating the risk of drug development, and of improving therapeutic outcomes and patient safety.

One aspect of the disclosure encompasses embodiments of a bifunctional nanoprobe for detecting hepatic injury generating a at least one of a reactive oxygen species and a reactive nitrogen species, said nanoprobe comprising: (i) a matrix core comprising: (a) a fluorescent superconducting polymer; and (b) a copolymer having a plurality of galactose moieties conjugated thereto, wherein the plurality of galactose moieties are disposed at the surface of the matrix core; (ii) a chemiluminescent sensor that in the presence of hydrogen peroxide can provide a chemical source of energy capable of inducing a detectable signal from a dye; and (iii) a fluorescent sensor that is decomposed when in the presence of ONOO or HOCl.

In embodiments of this aspect of the disclosure, the fluorescent superconducting polymer can be selected from the group consisting of: a poly(phenylene-vinylene) (PPV) derivative, a polyfluorene (PF) derivative, and a polythiophene (PT) derivative.

In embodiments of this aspect of the disclosure, the fluorescent superconducting polymer can be selected from the group consisting of: poly[2-methoxy-5-(2-ethylhexyloxy)-1,4-phenylenevinylene] (MEH-PPV), poly{[2-[2',5'-bis(2"-ethylhexyloxy)phenyl]-1,4-phenylenevinylene]-co-[2-methoxy-5-(2'-ethylhexyloxy)-1,4-phenylenevinylene]}, poly[(9,9-dioctyl-2,7-divinylenefluorenylene)-alt-co-{2-methoxy-5-(2-ethylhexyloxy)-1,4-phenylene}], poly[2,7-(9,9-di-octyl-fluorene)-alt-4,7-bis(thiophen-2-yl)benzo-2,1,3-thiadiazole], poly[(9,9-dioctyl-2,7-divinylenefluorenylene)-alt-co-(9,10-anthracene)], poly[{9,9-dihexyl-2,7-bis(1-cyanovinylene)fluorenylene}-alt-co-{2,5-bis(N,N'-diphenylamino)-1,4-phenylene}], poly[(9,9-dioctylfluorenyl-2,7-diyl)-alt-(benzo[2,1,3]thiadiazol-4,7-diyl)], poly[2,7-(9,9-di-octyl-fluorene)-alt-4,7-bis(thiophen-2-yl)benzo-2,1,3-thiadiazole], poly[(9,9-dioctylfluorenyl-2,7-diyl)-co-(1,4-diphenylene-vinyl-ene-2-methoxy-5-{2-ethylhexyloxy}-benzene)]; poly[(9,9-dioctyl-2,7-divinylenefluorenylene)-alt-co-(1,4-phenylene)], poly[(9,9-dioctylfluorenyl-2,7-diyl)-co-(N,N'-diphenyl)-N,N'-di(p-butylphenyl)-1,4-diamino-benzene)], poly[(9,9-dihexylfluorenyl-2,7-diyl)-co-(9,10-anthracene)], poly[(9,9-dioctylfluorenyl-2,7-diyl)-alt-co-(N,N'-bis{4-butyl-phenyl}-benzidineN,N'-{1,4-diphenylene})], poly[(9,9-dihexylfluorenyl-2,7-diyl)-alt-co-(2-methoxy-5-{2-ethylhexyloxy}-1,4-phenylene)], poly[(9,9-dihexylfluorenyl-2,7-diyl)-alt-co-(9,9'-spiro-bifluorene-2,7-diyl)], poly[(9,9-dihexylfluorenyl-2,7-diyl)-alt-co-(bithiophene)], poly[(9,9-dihexylfluorenyl-2,7-diyl)-alt-co-(bithiophene)], and poly[(9,9-dioctylfluorenyl-2,7-diyl)-co-(4,4'-(N-(p-butyl-phenyl))diphenylamine)], poly[2-methoxy-5-(2-ethylhexyl-oxy)-1,4-phenylene-vinylene], poly[2-methoxy-5-(2-ethylhexyloxy)-1,4-(1-cyanovinylene-1,4-phenylene)], poly[{2-methoxy-5-(2-ethylhexyloxy)-1,4-(1-cyanovinylenephenylene)}-co-{2,5-bis(N,N'-diphenylamino)-1,4-phenylene}]); poly[2,6-(4,4'-bis(2-ethylhexyl)dithieno[3,2-b:2',3'-d]silole)-alt-4,7(2,1,3-benzothiadiazole)], poly[N-9'-heptadecanyl-2,7-carbazole-alt-5,5-(4',7'-di-2-thienyl-2',1',3'-benzothiadiazole)], poly[3-hexylthiophene-2,5-diyl], poly[2,5-bis(3-dodecylthiophen- 2-yl)thieno[3,2-b]thiophene], poly[3-decylthiophene-2,5-diyl], poly[3-methyl-4-decylthiophene-2,5-diyl], poly[3-methyl-4-octylthiophene-2,5-diyl], poly[3-methyl-4-hexylthiophene-2,5-diyl], poly[3-methyl-4-butylthiophene-2,5-diyl], poly[3-decylthiophene-2,5-diyl], and poly[3-octylthiophene-2,5-diyl], and poly[3-butylthiophene-2,5-diyl].

In embodiments of this aspect of the disclosure, the fluorescent superconducting polymer can be poly[2,7-(9,9-di-octyl-fluorene)-alt-4,7-bis(thiophen-2-yl)benzo-2,1,3-thiadiazole].

In embodiments of this aspect of the disclosure, the copolymer can comprise polystyrene and polyethylene glycol monomers, wherein the plurality of galactose moieties can be conjugated to the polyethylene glycol.

In embodiments of this aspect of the disclosure, the fluorescent sensor can be 2-[4'-(β-carboxyethylthio)-7'-(1",3",3"-trimethylindolenine)-3',5'-trimethyleneheptatrien-1-yl]-1,3,3-trimethylindolenium perchlorate (IR775S) or diaminocyanine.

In embodiments of this aspect of the disclosure, the chemiluminescent sensor can be bis-(2,4,5-trichloro-6-(pentyloxycarbonyl)phenyl)oxalate (CPPO), 6-(4-methoxyphenyl)-2-methyl-3,7-dihydroimidazo[1,2-a]pyrazin-3-one (MCLA), or 2-methyl-6-phenyl-3,7-dihydroimidazo[1,2-a]pyrazin-3-one (CLA).

Another aspect of the disclosure encompasses embodiments of a method of detecting hepatic injury in a human or non-human subject, said method comprising the steps of: (a) delivering to the liver of to a human or non-human subject a pharmaceutically acceptable composition comprising a bifunctional nanoprobe for detecting hepatic injury and a pharmaceutically acceptable carrier, said nanoprobe comprising: (i) a matrix core comprising: (a) a fluorescent superconducting polymer; and (b) a copolymer having a plurality of galactose moieties conjugated thereto, wherein the plurality of galactose moieties are disposed at the surface of the matrix core; (ii) a chemiluminescent sensor that in the presence of hydrogen peroxide provides a chemical source of energy capable of inducing a detectable signal from a dye; and (iii) a fluorescent sensor that is decomposed when in the presence of ONOO or HOCl; (b) irradiating the recipient human or non-human subject with an excitation light at a wavelength selected as inducing a fluorescent emission by the fluorescent superconducting polymer; (c) determining the intensities of a first detectable signal at a first wavelength and a second detectable signal at a second wavelength emitted by the fluorescent sensor, wherein the ratio of said intensities, when differing from the ratio obtained from the bifunctional nanoprobe before delivering to the human or non-human subject, indicates an hepatic injury in the subject that generates a reactive nitrogen species; and (d) determining the intensity of a detectable signal emitted from the chemiluminescent sensor, wherein the emission of said detectable signal indicates an hepatic injury in the subject that generates a reactive oxygen species.

In embodiments of this aspect of the disclosure, the intensities of the detectable signals emitted from the fluorescent sensor and the chemiluminescent sensor can be converted to an image overlay of the body of the human or non-human subject, thereby locating a site of hepatic injury in said subject.

In embodiments of this aspect of the disclosure, the method can further comprise the steps of: (1) administering to the human or non-human subject a dose of a compound, wherein the compound is a therapeutic agent, a candidate therapeutic agent, or a compound suspected of having a hepatotoxic effect on the liver of the recipient subject; and (2) repeating steps (a)-(d), whereby the detection of an hepatic injury in the subject that generates a reactive oxygen and/or nitrogen species indicates that the compound has an hepatotoxic effect on the liver of the human or non-human subject.

In embodiments of this aspect of the disclosure, the fluorescent superconducting polymer can be selected from the group consisting of: a poly(phenylene-vinylene) (PPV) derivative, a polyfluorene (PF) Derivative, and a polythiophene (PT) derivative.

In embodiments of this aspect of the disclosure, the fluorescent superconducting polymer can be selected from the group consisting of: poly[(9,9-dioctyl-2,7-divinylene-fluorenylene)-alt-co-{2-methoxy-5-(2-ethylhexyloxy)-1,4-phenylene}], poly[2,7-(9,9-di-octyl-fluorene)-alt-4,7-bis(thiophen-2-yl)benzo-2,1,3-thiadiazole], poly[(9,9-dioctyl-2,7-divinylenefluorenylene)-alt-co-(9,10-anthracene)], poly[{9,9-dihexyl-2,7-bis(1-cyanovinylene)fluorenylene}-alt-co-{2,5-bis(N,N'-diphenylamino)-1,4-phenylene}], poly[(9,9-dioctylfluorenyl-2,7-diyl)-alt-(benzo[2,1,3]thiadiazol-4,7-diyl)], poly[2,7-(9,9-di-octyl-fluorene)-alt-4,7-bis(thiophen-2-yl)benzo-2,1,3-thiadiazole], poly[(9,9-dioctylfluorenyl-2,7-diyl)-co-(1,4-diphenylene-vinyl-ene-2-methoxy-5-{2-ethylhexyloxy}-benzene)]; poly[(9,9-dioctyl-2,7-divinylenefluorenylene)-alt-co-(1,4-phenylene)], poly[(9,9-dioctylfluorenyl-2,7-diyl)-co-(N,N'-diphenyl)-N,N'-di(p-butylphenyl)-1,4-diamino-benzene)], poly[(9,9-dihexylfluorenyl-2,7-diyl)-co-(9,10-anthracene)], poly[(9,9-dioctylfluorenyl-2,7-diyl)-alt-co-(N,N'-bis{4-butylphenyl}-benzidineN,N'-{1,4-diphenylene})], poly[(9,9-dihexylfluorenyl-2,7-diyl)-alt-co-(2-methoxy-5-{2-ethylhexyloxy}-1,4-phenylene)], poly[(9,9-dihexylfluorenyl-2,7-diyl)-alt-co-(9,9'-spiro-bifluorene-2,7-diyl)], poly[(9,9-dihexylfluorenyl-2,7-diyl)-alt-co-(bithiophene)], poly[(9,9-dihexylfluorenyl-2,7-diyl)-alt-co-(bithiophene)], and poly[(9,9-dioctylfluorenyl-2,7-diyl)-co-(4,4'-(N-p-butyl-phenyl)diphenylamine)]; poly[2-methoxy-5-(2-ethylhexyloxy)-1,4-phenylenevinylene] (MEH-PPV), poly{[2-[2',5'-bis(2"-ethylhexyloxy)phenyl]-1,4-phenylenevinylene]-co-[2-methoxy-5-(2'-ethylhexyloxy)-1,4-phenylenevinylene]}, poly[2-methoxy-5-(2-ethylhexyloxy)-1,4-(1-cyanovinylene-1,4-phenylene)], and poly[{2-methoxy-5-(2-ethylhexyloxy)-1,4-(1-cyanovinylenephenyl-ene)}-co-{2,5-bis(N,N'-diphenylamino)-1,4-phenylene}]); and (c) poly[2,6-(4,4'-bis(2-ethylhexyl)dithieno[3,2-b:2',3'-d]silol-eyalt-4,7(2,1,3-benzothiadiazole)], poly[N-9'-heptadecanyl-2,7-carbazole-alt-5,5-(4',7'-di-2-thienyl-2',1',3'-benzothiadiazole)], poly[3-hexylthiophene-2,5-diyl], poly[2,5-bis(3-dodecylthiophen-2-yl)thieno[3,2-b]thiophene], poly[3-decylthiophene-2,5-diyl], poly[3-methyl-4-decylthiophene-2,5-diyl], poly[3-methyl-4-octylthiophene-2,5-diyl], poly[3-methyl-4-hexylthiophene-2,5-diyl], poly[3-methyl-4-butylthiophene-2,5-diyl], poly[3-decylthiophene-2,5-diyl], and poly[3-octylthiophene-2,5-diyl], poly[3-butylthiophene-2,5-diyl].

In embodiments of this aspect of the disclosure, the fluorescent superconducting polymer can be poly[2,7-(9,9-di-octyl-fluorene)-alt-4,7-bis(thiophen-2-yl)benzo-2,1,3-thiadiazole].

In embodiments of this aspect of the disclosure, the copolymer can be comprised of polystyrene and polyethylene glycol monomers, wherein the plurality of galactose moieties can be conjugated to the polyethylene glycol.

In embodiments of this aspect of the disclosure, the fluorescent sensor can be 2-[4'-(β-carboxyethylthio)-7'-(1", 3",3"-trimethylindolenine)-3',5'-trimethyleneheptatrien-1-yl]-1,3,3-trimethylindolenium perchlorate (IR775S) or diaminocyanine.

In embodiments of this aspect of the disclosure, the chemiluminescent sensor can be bis-(2,4,5-trichloro-6-(pentyloxycarbonyl)phenyl)oxalate (CPPO), 6-(4-Methoxyphenyl)-2-methyl-3,7-dihydroimidazo[1,2-a]pyrazin-3-one (MCLA), or 2-Methyl-6-phenyl-3,7-dihydroimidazo[1,2-a]pyrazin-3-one (CLA).

Yet another aspect of the disclosure encompasses embodiments of a method for determining if a compound is hepatotoxic, said method comprising the steps of: (a) delivering to the liver of to a human or non-human subject a pharmaceutically acceptable composition comprising a bifunctional nanoprobe for detecting hepatic injury and a pharmaceutically acceptable carrier, said nanoprobe comprising: (i) a matrix core comprising: (a) a fluorescent superconducting polymer, wherein the fluorescent superconducting polymer is poly[2,7-(9,9-di-octyl-fluorene)-alt-4,7-bis(thiophen-2-yl)benzo-2,1,3-thiadiazole]; and (b) a copolymer having a plurality of galactose moieties conjugated thereto, wherein the copolymer is comprised of polystyrene and polyethylene glycol monomers, and wherein the plurality of galactose moieties are conjugated to the polyethylene glycol so as to dispose the plurality of galactose moieties at the surface of the matrix core; (ii) a chemiluminescent sensor that in the presence of hydrogen peroxide provides a chemical source of energy capable of inducing a detectable signal from a dye, wherein the chemiluminescent sensor is bis-(2,4,5-trichloro-6-(pentyloxycarbonyl)phenyl)oxalate (CPPO); and (iii) a fluorescent sensor that is decomposed when in the presence of ONOO or HOCl, wherein the fluorescent sensor is 2-[4'-(β-carboxyethylthio)-7'-(1",3",3"-trimethylindolenine)-3',5'-trimethyleneheptatrien-1-yl]-1,3,3-trimethylindolenium perchlorate (IR775S); (b) irradiating the recipient human or non-human subject with an excitation light at a wavelength selected as inducing a fluorescent emission by the fluorescent superconducting polymer; (c) determining the intensities of a first detectable signal at a first wavelength and a second detectable signal at a second wavelength emitted by the fluorescent sensor, wherein the ratio of said intensities, when differing from the ratio obtained from the bifunctional nanoprobe before delivering to the human or non-human subject, indicates an hepatic injury in the subject that generates a reactive nitrogen species; and (d) determining the intensity of a detectable signal emitted from the chemiluminescent sensor, wherein the emission of said detectable signal indicates an hepatic injury in the subject that generates a reactive oxygen species; (e) administering to the human or non-human subject a dose of a compound, wherein the compound is a therapeutic agent, a candidate therapeutic agent, or a compound suspected of having a hepatotoxic effect on the liver of the recipient subject; and (f) repeating steps (a)-(d), whereby the detection of an hepatic injury in the subject that generates a reactive oxygen and/or nitrogen species indicates that the compound has an hepatotoxic effect on the liver of the human or non-human subject.

In embodiments of this aspect of the disclosure, the intensities of the detectable signals emitted from the fluorescent sensor and the chemiluminescent sensor are converted to an image overlay of the body of the human or non-human subject, thereby locating a site of hepatic injury in said subject.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLE

Example 1

Chemicals:

All chemicals were obtained from Sigma-Aldrich unless otherwise stated. $PEG_{COOH}$-g-PS ($M_n$=217,000, $M_w/M_n$=1.25) was from Polymer Source, and the number of branches of this polymer is 11 per 74 units of styrene backbone units. Ultrapure water and 1×PBS were purchased from Invitrogen. Poly[2,7-(9,9-dioctylfluorene)-alt-4,7-bis(thiophen-2-yl)benzo-2,1,3-thiadiazole] (PFODBT) ($M_w$=10,000-50,000) were from Sigma-Aldrich. The RONS-sensitive dye (IR775S) was synthesized according to Nasr et al., (2011) *Adv. Ther.* 28: 842-856, incorporated herein by reference in its entirety.

Example 2

Synthesis of Amino Galactoside.

Azidoethyl diethylene glycol (816 mg, 4.658 mmol) and glycosyl donor 2,3,4,6-tetra-O-acetyl-D-galactopyranosyl trichloroacetamide (5.00 g, 9.316 mmol) were dissolved in dry dichloromethane (50 mL). Molecular sieves (5.0 g, 4 Å) were added and the mixture was stirred for 1 h at room temperature under argon. The reaction mixture was cooled to 0° C., and trimethylsilyl trifluoromethanesulfonate (84 μL, 0.466 mmol) was added slowly. The reaction was allowed to warm to room temperature and completed in 1 h. Triethylamine (100 μL) was added to neutralize the solution, and column chromatography gave the titled compound as a yellowish solid. The product was dissolved in methanolic solution of sodium methoxide (10 mM, 50 mL), and stirred for 30 min at room temperature. Triphenylphosphine (1.22 g, 4.658 mmol) was then added and the reaction mixture was stirred overnight at room temperature. Methanol was removed by rotary evaporation and the resulting residue was purified by HPLC. Lyophilization gave the product as yellowish syrup (520 mg, β only, 36% over three steps). $^1$H NMR (400 MHz, $d_6$-DMSO): δ 4.88, 4.75, 4.71, 4.61, 4.55, 4.48, 4.44, 4.28, 4.19, 4.09 (β isomer, H-1), 3.85, 3.74, 3.70-3.20, 2.95 ($CH_2NH_2$). ESI MS calcd for $C_{12}H_{26}NO_8$ (M+H): 311.17, found: 311.17.

Example 3

Synthesis of PS-PEG-Gal:

$PEG_{COOH}$-g-PS (50 mg), amino galactoside (8 mg), O-benzotriazole-N,N,N',N'-tetramethyl-uronium-hexafluoro-phosphate (HBTU) (9.2 mg), and N-hydroxy-benzotriazole (HOBt) (3.28 mg) were dissolved in DMF (0.5 mL). Then, N,N-Diisopropylethylamine (DIPEA) (10 μL) was added, and the mixture was stirred at room temperature for 24 h. The reaction mixture was poured into diethyl ether, and the precipitate was dissolved in water. To remove the residual small molecule reagents, the aqueous solution was washed five times with deionized-water using a 30 K centrifugal filter unit (Millipore) under centrifugation at 4,000 rpm for 3 min at 4° C. After freeze-drying, the product was obtained as white power. The amount of galactose grafted to the polystyrene was quantified to be 0.4% per styrene ring ($^1$H-NMR in $d_6$-DMSO).

Example 4

Preparation of CF-SPNs:

A THF solution (2 mL) of PFODBT (0.25 mg), (PS-PEG-Gal (0.5 mg), CPPO (1 mg) and IR775S (2.5 μg) was rapidly injected into distilled-deionized water (10 mL) under continuous sonication. After sonication for additional 2 min, THF was evaporated at 40° C. under nitrogen atmosphere. The aqueous solution was filtered through a polyvinylidene fluoride (PVDF) syringe driven filter (0.22 μm) (Millipore), and washed three times using a 30 K centrifugal filter unit (Millipore) under centrifugation at 4,000 rpm for 3 min at 4° C. The nanoparticle solution was finally concentrated to 5 mg/mL by ultrafiltration and used immediately for in vitro and in vivo experiments.

Example 5

Optical Responses Towards Different RONS in Solution.

$H_2O_2$, $ONOO^-$, $OCl-$, and $O_2^{.-}$, stock solutions were prepared by directly diluting commercially available $H_2O_2$, NaONOO, NaOCl, and $KO_2$ respectively. NO was generated from diethylamine NONOate. .OH was generated by the Fenton reaction between $H_2O_2$ and $Fe(ClO_4)_2$. $^1O_2$ was produced from the $H_2O_2$/molybdate ions ($Na_2MoO_4$) system. The fluorescence intensities ($\lambda_{ex}$=580 nm, $\lambda_{em}$=680 or 820 nm) of the CF-SPN solution (5 μg/mL) in PBS (30 mM, pH=7.4) were measured 5 min after the addition of RONS (5 μM) to determine the intensity enhancement. Chemiluminescence intensities were measured by IVIS with open filter. PBS used for these experiments was purged with $N_2$ for 1 h before the measurement.

Example 6

In Vitro Characterization of CF-SPN:

CF-SPN (10 μg/mL) in PBS (30 mM, pH=7.4) was placed in a black 96-well plate. After addition of excess $H_2O_2$ (50 mM), the chemiluminescence was continuously acquired using an IVIS® Spectrum pre-clinical in vivo imaging system (PerkinElmer, Mass., USA) with open filter and autoexposure setting. The intensities were calculated with ROI and plotted as a function of time.

The stability of CF-SPN fluorescence and luminescence was determined by diluting CF-SPNs to a final concentration of 5 μg/mL in undiluted mouse serum and incubating at 37° C. for the indicated time period. Both fluorescence and luminescence imaging was performed using an IVIS® Spectrum pre-clinical in vivo imaging system. Luminescence images were acquired for 3 min with open filter, and fluorescence images were acquired using autoexposure with excitation of 580±10 nm, and emission at both 680±10 nm and 820±10 nm.

To determine the depth of signal penetration through tissue-like gel phantoms, CF-SPN solution (5 μg/mL) in PBS (30 mM, pH=7.4) was placed in a black 96-well plate. Gel phantoms, as described by Shuhendler et al., ((2011) *ACS Nano* 5: 1958-1966) incorporated herein by reference in its entirety, and composed of porcine gelatin, bovine hemoglobin, intralipid and $NaN_3$ in Tris-buffered saline at final concentrations of 10% w/v, 170 μM, 1% v/v, and 15 mM, respectively, were overlaid on top of the wells at the desired gel thickness. Images were acquired using an IVIS® Spectrum imaging system using luminescence acquisition mode with open filter and autoexposure setting.

Example 7

Animal Models of Drug-Induced Hepatotoxicity:

All animal experiments involved 8-10 week old female nude mice (Charles River Laboratories International, Inc., Mass., USA). Animals were fasted for 8 h prior to imaging for all drug-induced hepatotoxicity imaging. Animals were treated intraperitoneally with sterilized saline solutions of APAP (10 mg/mL) or INH (10 mg/mL) and were then anesthetized with intraperitoneal injection of 100 mg/kg ketamine and 10 mg/mL xylazine. A tail vein catheter was inserted, and the mice were placed in an IVIS® Spectrum imaging system. Fifteen minutes after the administration of drug, 0.8 mg CF-SPN was injected intravenously through the tail vein catheter, and imaging began immediately. Luminescence images were acquired for 3 min with an open filter, and fluorescence images were acquired using autoexposure with excitation of 580±10 nm, and emission at both 680±10 nm and 820±10 nm.

Animals were imaged longitudinally for the indicated lengths of time, warmed until observable sternal recumbence, and then returned to their cage. Animals were euthanized 180 min following drug treatment, and their livers were resected and placed into buffered formalin for histological examination. A separate set of animals was fasted, treated with drug, and their livers were resected after euthanasia to provide tissues for histological examination 45 min following drug treatment.

For inhibitor studies, animals were treated with 200 mg/kg of GSH intravenously 5 min prior to drug treatment (James et al., (2003) *Toxicol. Sci.* 75: 458-467), with 0.2 mg/kg t-1,2-DCE intraperitoneally 2 h prior to drug treatment (Jackson et al., (2000) *Toxicol. Sci.* 55: 266-273), or with 100 mg/kg 1-ABT intraperitoneally 12 and 24 h prior to drug treatment (as described in Jackson et al., (2000) *Toxicol. Sci.* 55: 266-273).

For the assessment of APAP-induced hepatotoxicity with luminol, mice were treated as described, and injected intravenously with 0.2 mg luminol in 100 μL saline adjusted to pH 8.0 with $NaHCO_3$.

To assess the production of hepatic oxidative or nitrosative stress in vivo following administration of SPN, mice were anesthetized by ketamine/xylazine injection and fitted with tail vein catheters. Either saline or 0.8 mg/kg Gal-SPN were then administered intravenously, followed immediately by 0.8 mg/kg CF-SPN.

To determine the biodistribution of Gal-SPN and PEG-SPN, 0.8 mg/kg of nanoparticles were administered intravenously to mice, which were euthanized 45 min later. Thigh muscle, lungs, heart, liver, kidneys, and spleen were resected, placed onto black paper, and imaged using the IVIS® Spectrum system with excitation at 580±10 nm and emission at 680±10 nm.

Example 8

Histology.

All tissues were embedded in paraffin prior to 10 micron sectioning. Histology samples were stained by hematoxylin and eosin under standard protocols. Immunohistochemistry samples were processed using an anti-nitrotyrosine primary antibody (Life Technologies Inc., NY, USA) at 1:500 dilution, with color development according to the protocol described in the DAKO LSB+ kit. Endogenous peroxidases were quenched prior to processing. TUNEL staining was performed according to the manufacturer instructions using the ApopTag Plus Peroxidase In Situ Apoptosis Kit (EMD Millipore, Mass., USA). All images were acquired using an Olympus IX2-UCB (Olympus America Inc., PA, USA) inverted fluorescence microscope equipped with a Nuance (CRi Inc., MA, USA) hyperspectral camera capable of brightfield full color imaging.

Example 9

Data Analysis.

Luminescence data was processed using Living Image software (v. 4.3.1, Perkin Elmer, Mass., USA) for all experiments, in addition to fluorescence data for biodistribution experiments. For fluorescent ratiometric mapping of liver intensity, image scale bars were normalized, with the scale set to a red color scheme.

Fluorescence images without photograph overlay were exported as TIFF, read into Matlab® (v. 8.0.0.783, The MathWorks Inc., CO, USA) where the percent difference between the fluorescence intensity at 680 nm and 820 nm was mapped for the liver region of interest. To plot the fluorescence index (FL index) over time, fluorescence intensities of the liver region of interest were extracted for images acquired with emission at 680 nm and at 820 nm using Living Image software. The intensity values, measured in units of radiance efficiency, were exported to Excel® where the percent difference in emission intensity at 680 nm and 820 nm was calculated. Finally, the FL index was calculated as the ratio of the percent difference of drug treated animals to that of control animals. All statistical analyses were performed using Prism software (v. 5.0c, GraphPad Software Inc., CA, USA).

Example 10

Figure 14:
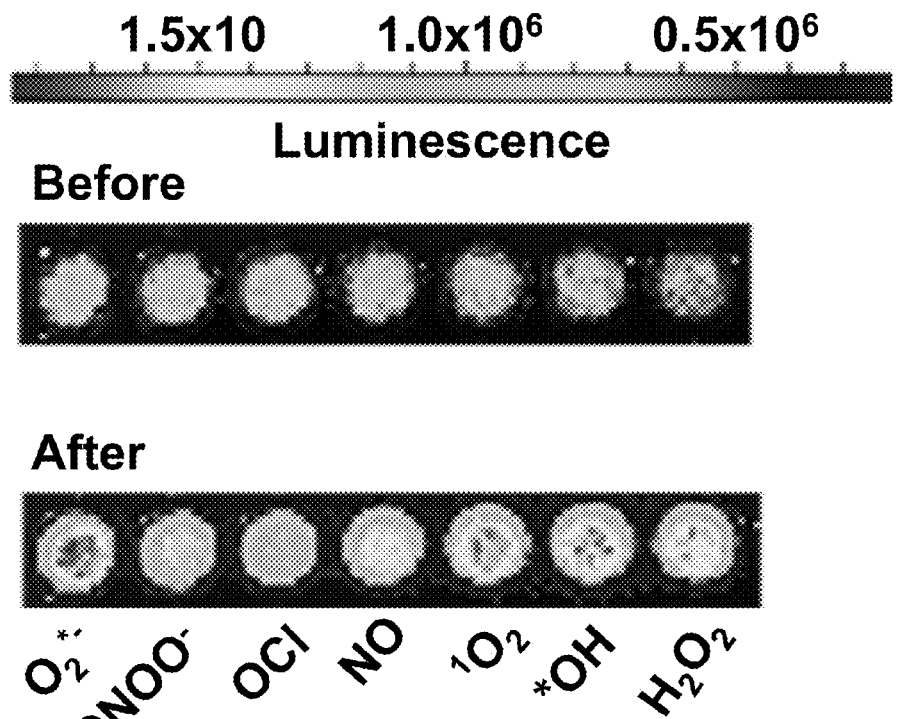
FIG. 14 illustrates the CRET reaction between MEH-PPV and MCLA in the presence of ROS.
Figure 15:
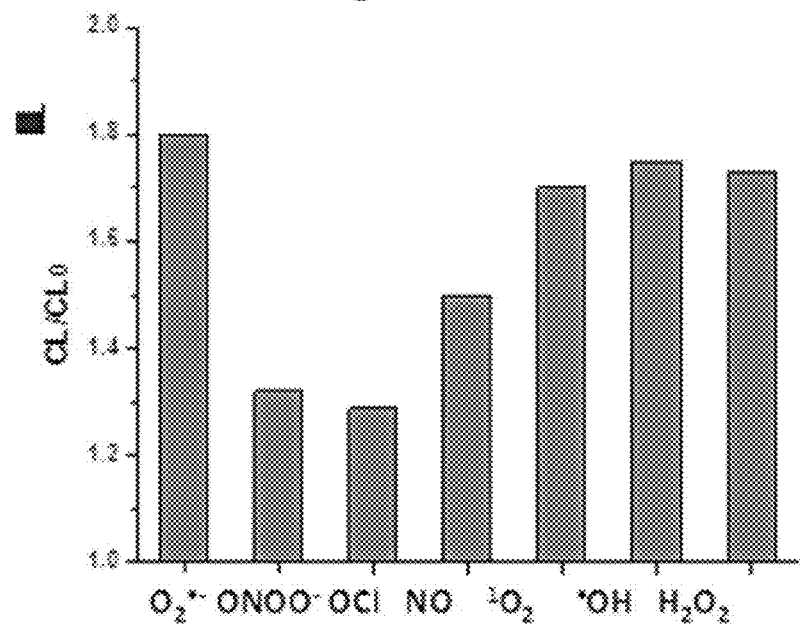
FIG. 15 illustrates the CRET reaction between MEH-PPV and MCLA in the presence of ROS.
Figure 16:
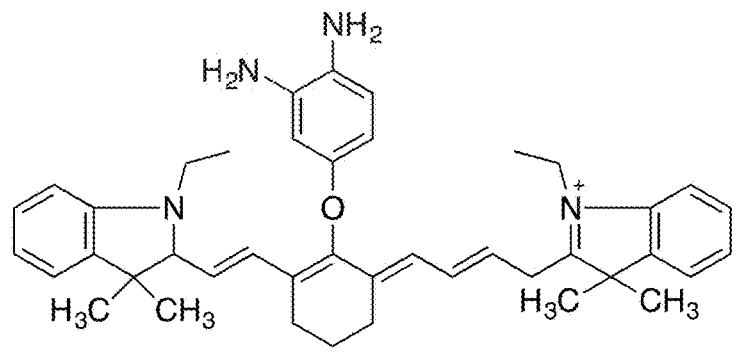
FIG. 16 illustrates the chemical structure of NO-sensitive diaminocyanine.

CRET between different pair of SP and chemiluminescence substrate was tested. As shown in FIGS. 14 and 15, efficient CRET can occur between Poly[2-methoxy-5-(2-ethylhexyloxy)-1,4-phenylenevinylene] (MEH-PPV) and 2-Methyl-6-phenyl-3,7-dihydroimidazo[1,2-a]pyrazin-3-one (MCLA), resulting in chemiluminescence in the presence of ROS. It is contemplated that similar reactions will occur with, for example, 6-(4-Methoxyphenyl)-2-methyl-3,7-dihydroimidazo[1,2-a]pyrazin-3-one Hydrochloride (CLA) and other derivatives of PPV such as poly{[2-[2',5'-bis(2"-ethylhexyloxy)phenyl]-1,4-phenylenevinylene]-co-[2-methoxy-5-(2'-ethylhexyloxy)-1,4-phenylenevinylene]}, Poly[2-methoxy-5-(3',7'-dimethyloctyloxy)-1,4-phenylenevinylene] (MDMO-PPV) and the like.

Example 11

Figure 17:
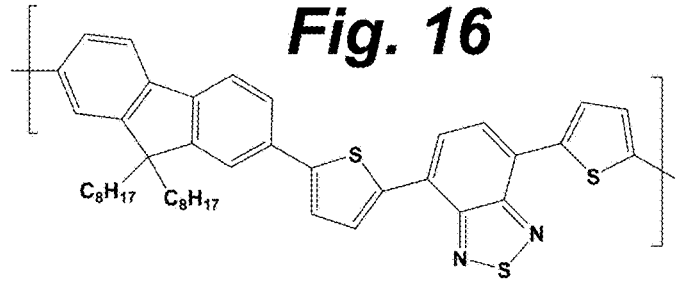
FIG. 17 illustrates the chemical structure of NO-sensitive PFODBT.

FRET was also examined between different pairs of SP and ROS-sensitive dye. In FIGS. 17 and 18 is show that nanoprobes with NO response can be obtained by doping diaminocyanine into an SPN.

What is claimed:

1. A bifunctional nanoprobe comprising:
   (i) a matrix core comprising:
      (a) a fluorescent superconducting polymer, wherein said polymer is a 9,9 diarylpolyfluorene polymer or a poly(p-phenylene vinylene) polymer; and
      (b) a copolymer comprised of polystyrene and polyethylene glycol monomers and having a plurality of galactose moieties conjugated to the polyethylene glycol and wherein the plurality of galactose moieties are disposed at the surface of the matrix core;
   (ii) a chemiluminescent sensor cleavable by hydrogen peroxide and selected from the group consisting of bis-(2,4,5-trichloro-6-(pentyloxycarbonyl)phenyl)oxalate (CPPO), 6-(4-methoxyphenyl)-2-methyl-3,7-dihydroimidazo[1,2-a]pyrazin-3-one (MCLA), and 2-methyl-6-phenyl-3,7-dihydroimidazo[1,2-a]pyrazin-3-one (CLA); and
   (iii) a fluorescent sensor, wherein said fluorescent sensor is 2-[4'-(β-carboxyethylthio)-7'-(1",3",3"-trimethylindolenine)-3',5'-trimethyleneheptatrien-1-yl]-1,3,3-trimethylindolenium perchlorate (IR775S) or diaminocyanine.

2. The nanoprobe of claim 1, wherein the 9,9 diarylpolyfluorene polymer is selected from the group consisting of: poly[(9,9-dioctyl-2,7-divinylenefluorenylene)-alt-co-{2-methoxy-5-(2-ethylhexyloxy)-1,4-phenylene}], poly[2,7-(9,9-di-octyl-fluorene)-alt-4,7-bis(thiophen-2-yl)benzo-2,1,3-thiadiazole], poly[(9,9-dioctyl-2,7-divinylenefluorenylene)-alt-co-(9,10-anthracene)], poly[{9,9-dihexyl-2,7-bis(1-cyanovinylene)fluorenylene}-alt-co-{2,5-bis(N,N'-diphenylamino)-1,4-phenylene}], poly[(9,9-dioctylfluorenyl-2,7-diyl)-alt-(benzo[2,1,3]thiadiazol-4,7-diyl)], poly[2,7-(9,9-di-octyl-fluorene)-alt-4,7-bis(thiophen-2-yl)benzo-2,1,3-thiadiazole], poly[(9,9-dioctylfluorenyl-2,7-diyl)-co-(1,4-diphenylene-vinyl-ene-2-methoxy-5-{2-ethylhexyloxy}-benzene)]; poly[(9,9-dioctyl-2,7-divinylenefluorenylene)-alt-co-(1,4-phenylene)], poly[(9,9-dioctylfluorenyl-2,7-diyl)-co-(N,N'-diphenyl)-N,N'-di(p-butylphenyl)-1,4-diamino-benzene)], poly[(9,9-dihexylfluorenyl-2,7-diyl)-co-(9,10-anthracene)], poly[(9,9-dioctylfluorenyl-2,7-diyl)-alt-co-(N,N'-bis{4-butyl-phenyl}-benzidineN,N'-{1,4-diphenylene})], poly[(9,9-dihexylfluorenyl-2,7-diyl)-alt-co-(2-methoxy-5-{2-ethylhexyloxy}-1,4-phenylene)], poly[(9,9-dihexylfluorenyl-2,7-diyl)-alt-co-(9,9'-spiro-bifluorene-2,7-diyl)], poly[(9,9-dihexylfluorenyl-2,7-diyl)-alt-co-(bithiophene)], poly[(9,9-dihexylfluorenyl-2,7-diyl)-alt-co-(bithiophene)], and poly[(9,9-dioctylfluorenyl-2,7-diyl)-co-(4,4'-(N-(p-butyl-phenyl))diphenylamine)].

3. The nanoprobe of claim 2, wherein the 9,9 diarylpolyfluorene polymer fluorescent superconducting polymer is poly[2,7-(9,9-di-octyl-fluorene)-alt-4,7-bis(thiophen-2-yl)benzo-2,1,3-thiadiazole].

4. The nanoprobe of claim 1, wherein the poly(p-phenylene vinylene) polymer is selected from the group consisting of: poly[2-methoxy-5-(2-ethylhexyloxy)-1,4-phenylenevinylene] (MEH-PPV), poly{[2-[2',5'-bis(2"- ethylhexyloxy)phenyl]-1,4-phenylenevinylene]-co-[2-methoxy-5-(2'-ethylhexyloxy)-1,4-phenylenevinylene]}, poly[2-methoxy-5-(2-ethylhexyloxy)-1,4-(1-cyanovinylene-1,4-phenylene)], and poly[{2-methoxy-5-(2-ethylhexyloxy)-1,4-(1-cyanovinylenephenylene)}-co-{2,5-bis(N,N'-diphenylamino)-1,4-phenylene}]).

5. A bifunctional nanoprobe comprising:
(i) a matrix core comprising:
   (a) a fluorescent superconducting polymer wherein said polymer is poly[2,7-(9,9-di-octyl-fluorene)-alt-4,7-bis(thiophen-2-yl)benzo-2,1,3-thiadiazole] or poly[2-methoxy-5-(2-ethylhexyloxy)-1,4-phenylenevinylene] (MEH-PPV); and
   (b) a copolymer comprised of polystyrene and polyethylene glycol monomers and having a plurality of galactose moieties conjugated to the polyethylene glycol and wherein the plurality of galactose moieties are disposed at the surface of the matrix core;
(ii) a chemiluminescent sensor selected from the group consisting of bis-(2,4,5-trichloro-6-(pentyloxycarbonyl)phenyl)oxalate (CPPO), 6-(4-methoxyphenyl)-2-methyl-3,7-dihydroimidazo[1,2-a]pyrazin-3-one (MCLA), and 2-methyl-6-phenyl-3,7-dihydroimidazo[1,2-a]pyrazin-3-one (CLA); and
(iii) a fluorescent sensor, wherein said fluorescent sensor is 2-[4'-(β-carboxyethylthio)-7'-(1",3",3"-trimethylindolenine)-3',5'-trimethyleneheptatrien-1-yl]-1,3,3-trimethylindolenium perchlorate (IR775S) or diaminocyanine.

6. The bifunctional nanoprobe of claim 5, said nanoprobe comprising:
(i) a matrix core comprising:
   (a) a fluorescent superconducting polymer comprising poly[2,7-(9,9-di-octyl-fluorene)-alt-4,7-bis(thiophen-2-yl)benzo-2,1,3-thiadiazole]; and
   (b) a copolymer consisting of polystyrene and polyethylene glycol monomers and having a plurality of galactose moieties conjugated to the polyethylene glycol and, wherein the plurality of galactose moieties are disposed at the surface of the matrix core;
(ii) a chemiluminescent sensor, wherein said sensor is bis-(2,4,5-trichloro-6-(pentyloxycarbonyl)phenyl)oxalate (CPPO); and
(iii) a fluorescent sensor, wherein said fluorescent sensor is 2-[4'-(β-carboxyethylthio)-7'-(1",3",3"-trimethylindolenine)-3',5'-trimethyleneheptatrien-1-yl]-1,3,3-trimethylindolenium perchlorate (IR775S).

* * * * *